United States Patent
Jishage et al.

(10) Patent No.: US 10,822,420 B2
(45) Date of Patent: Nov. 3, 2020

(54) GENE KNOCK-IN NON-HUMAN ANIMAL

(71) Applicant: CHUGAI SEIYAKU KABUSHIKI KAISHA, Tokyo (JP)

(72) Inventors: Koichi Jishage, Gotemba (JP); Otoya Ueda, Gotemba (JP)

(73) Assignee: CHUGAI SEIYAKU KABUSHIKI KAISHA, Kita-ku, Tokyo (JP)

( * ) Notice: Subject to any disclaimer, the term of this patent is extended or adjusted under 35 U.S.C. 154(b) by 0 days.

(21) Appl. No.: 14/427,355

(22) PCT Filed: Sep. 13, 2013

(86) PCT No.: PCT/JP2013/074882
§ 371 (c)(1),
(2) Date: Mar. 11, 2015

(87) PCT Pub. No.: WO2014/042251
PCT Pub. Date: Mar. 20, 2014

(65) Prior Publication Data
US 2015/0225481 A1     Aug. 13, 2015

(30) Foreign Application Priority Data

Sep. 13, 2012 (JP) ................................. 2012-201299

(51) Int. Cl.
*A61K 49/00* (2006.01)
*G01N 33/68* (2006.01)
(Continued)

(52) U.S. Cl.
CPC ...... *C07K 16/2866* (2013.01); *A01K 67/0278* (2013.01); *A61K 49/0008* (2013.01);
(Continued)

(58) Field of Classification Search
None
See application file for complete search history.

(56) References Cited

U.S. PATENT DOCUMENTS 7,422,889 B2 * 9/2008 Sauer ................... C12N 9/00
435/194
10,433,528 B2 * 10/2019 Wang ................. C12N 15/907
(Continued)

FOREIGN PATENT DOCUMENTS

| WO |       02/094016 A1 | 11/2002 |             |
|----|--------------------|---------|-------------|
| WO | WO 2012/056457     | * 5/2012 | ........... A61K 48/00 |
| WO |      2013/047729 A1 | 4/2013  |             |

OTHER PUBLICATIONS

Semotok et al., *Drosophila* Maternal Hsp83 mRNA Destabilization Is Directed by Multiple SMAUG Recognition Elements in the Open Reading Frame. Molecular and Cellular Biology, Nov. 2008, p. 6757-6772.*

(Continued)

*Primary Examiner* — Christopher M Babic
*Assistant Examiner* — Arthur S Leonard
(74) *Attorney, Agent, or Firm* — Sughrue Mion, PLLC

(57) ABSTRACT

The present invention provides a non-human animal in which a DNA comprising an hp7 sequence-encoding DNA and a poly A addition signal-encoding DNA added on the 3' side of a DNA encoding an arbitrary foreign gene is inserted in the same reading frame as that of an arbitrary target gene present on the genome of the non-human animal.

16 Claims, 13 Drawing Sheets
(9 of 13 Drawing Sheet(s) Filed in Color)
Specification includes a Sequence Listing.

(51) Int. Cl.
    *C07K 16/28* (2006.01)
    *A01K 67/027* (2006.01)
    *G01N 33/50* (2006.01)
    *C07K 14/715* (2006.01)

(52) U.S. Cl.
    CPC ..... *C07K 14/7155* (2013.01); *G01N 33/5088* (2013.01); *G01N 33/6854* (2013.01); *G01N 33/6869* (2013.01); *A01K 2217/072* (2013.01); *A01K 2227/105* (2013.01); *A01K 2267/0387* (2013.01); *C07K 2317/24* (2013.01); *G01N 2333/7155* (2013.01); *G01N 2800/24* (2013.01)

(56) References Cited

U.S. PATENT DOCUMENTS

2004/0244063 A1    12/2004    Habu et al.
2014/0255398 A1    9/2014    Igawa et al.

OTHER PUBLICATIONS

Willinger et al., Improving human hemato-lymphoid system mice by cytokine knock-in gene replacement. Trends in Immunology Jul. 2011, vol. 32, No. 7, p. 321-327.*
Peters et al., The function of the soluble IL-6 receptor in vivo. Immunol Lett. Dec. 1996;54(2-3):177-84.*
Fuke et al., Role of poly (A) tail as an identity element for mRNA nuclear export. Nucleic Acids Research, 2008, vol. 36, No. 3 1037-1049.*
Huang et al., Role of Polyadenylation in Nucleocytoplasmic Transport of mRNA. Molecular and Cellular Biology, Apr. 1996, p. 1534-1542 vol. 16, No. 4 (Year: 1996).*
Rongvaux et al., Human thrombopoietin knockin mice efficiently support human hematopoiesis in vivo. PNAS, 2011, 108:2378-2383. (Year: 2011).*
Alignment human IL6-R and Mus IL6-R. https://embnet.vital-it.ch/software/LALIGN_form.html (Year: 2018).*
Alignment human IL6-R and Fish IL6-R. https://embnet.vital-it.ch/software/LALIGN_form.html (Year: 2018).*
Nobuyuki Udagawa et al., "Interleukin (IL)-6 Induction of Osteoclast Differentiation Depends on IL-6 Receptors Expressed on Osteoblastic Cells But Not on Osteoclast Progenitors", J. Exp. Med., Nov. 1995, pp. 1461-1468, vol. 182, No. 5.
Ralph L. Brinster et al., "Introns increase transcriptional efficiency in transgenic mice", Proc. Natl. Acad. Sci. USA, Feb. 1988, pp. 836-840, vol. 85.
Toshiaki Shigeoka et al., "Evidence that the Upf1-related molecular motor scans the 3'-UTR to ensure mRNA integrity", Nucleic Acids Research, 2012, pp. 1-11, doi: 10.1093/nar/gks344.
Shigeoka et al., "Evidence that the Upf1-related molecular motor scans the 3∝-UTR to ensure mRNA integrity", Nucleic Acids Research, 2012, pp. 6887-6897, vol. 40, No. 14, doi: 10.1093/nar/gks344.
Marilyn Kozak, "Circumstances and Mechanisms of Inhibition of Translation by Secondary Structure in Eucaryotic mRNAs", Molecular and Cellular Biology, Nov. 1989, pp. 5134-5142, vol. 9, No. 11.
Yoshiyuki Osugi et al., "Pharmacological and clinical profile of humanized anti-human IL-6 receptor antibody (tocilizumab), a novel therapeutic drug for Castleman's disease", Folia Pharmacologica Japonica, 2005, pp. 419-425, vol. 126.
International Search Report for PCT/JP2013/074882 dated Nov. 5, 2013.
International Preliminary Examination Report for PCT/JP2013/074882 dated Mar. 17, 2015, with Written Opinion.

* cited by examiner

SEQUENCE LISTING

```
<160> NUMBER OF SEQ ID NOS: 15

<210> SEQ ID NO 1
<211> LENGTH: 40
<212> TYPE: DNA
<213> ORGANISM: Artificial Sequence
<220> FEATURE:
<223> OTHER INFORMATION: hp7 sequence

<400> SEQUENCE: 1
ggggcgcgtg gtggcggctg cagccgccac cacgcgcccc                              40

<210> SEQ ID NO 2
<211> LENGTH: 34
<212> TYPE: DNA
<213> ORGANISM: Bacteriophage P1

<400> SEQUENCE: 2
ataacttcgt atagcataca ttatacgaag ttat                                    34

<210> SEQ ID NO 3
<211> LENGTH: 21
<212> TYPE: DNA
<213> ORGANISM: Artificial Sequence
<220> FEATURE:
<223> OTHER INFORMATION: Artificially synthesized primer sequence
```

```
<400> SEQUENCE: 3
acagggcctt agactcacag c                                              21

<210> SEQ ID NO 4
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 4
aacttgctcc cgacactact gg                                             22

<210> SEQ ID NO 5
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 5
tctgcagtag ccttcaaaga gc                                             22

<210> SEQ ID NO 6
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 6
aaccagacag tgtcacattc c                                              21

<210> SEQ ID NO 7
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 7
cccggctgcg gagccgctct gc                                             22

<210> SEQ ID NO 8
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 8
acagtgatgc tggaggtcct t                                              21

<210> SEQ ID NO 9
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 9
agcaacaccg tgaactcctt tg                                             22
```

```
<210> SEQ ID NO 10
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 10
tctgcagtag ccttcaaaga gc                                            22

<210> SEQ ID NO 11
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 11
aaccagacag tgtcacattc c                                             21

<210> SEQ ID NO 12
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 12
acctcttcag aacgaattga caaa                                          24

<210> SEQ ID NO 13
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 13
agctgcgcag aatgagatga gttgt                                         25

<210> SEQ ID NO 14
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 14
aagtcgctgc ctttatttag gtcttccaac taacc                              35

<210> SEQ ID NO 15
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 15
ttcagtgaca acgtcgagca cagctgc                                       27
```

GENE KNOCK-IN NON-HUMAN ANIMAL

CROSS REFERENCE TO RELATED APPLICATIONS

This application is a National Stage of International Application No. PCT/JP2013/074882 filed Sep. 13, 2013, claiming priority based on Japanese Patent Application No. 2012-201299 filed Sep. 13, 2012, the contents of all of which are incorporated herein by reference in their entirety.

TECHNICAL FIELD

The present invention relates to a gene knock-in non-human animal and a method for evaluating a compound using the gene knock-in non-human animal.

BACKGROUND ART

As a large number of therapeutic agents highly specific for molecular targets, such as antibody drugs, have been developed, there is a growing demand for humanized non-human animals such as humanized mice for more proper preclinical evaluation of the therapeutic agents. So-called transgenic mice which are mice genetically modified to express human genes and a gene targeting method which involves replacing mouse genes with human genes are widely known as approaches of preparing humanized mice. A large number of humanized mice prepared by such approaches have been reported. As in the transgenic mice, however, mice merely containing vectors for expression of human genes often fail to exhibit expected expression patterns. For example, a mouse allowed to overexpress a human interleukin-6 (IL-6) receptor gene using a pCAGGS vector has been reported (Non Patent Literature 1). This transgenic mouse ectopically expresses the human IL-6 (hIL-6) receptor in tissues or cells other than the original expression sites, owing to the high expression level of the hIL-6 receptor attributed to its strong promoter. The transgenic mouse also expresses the mouse endogenous IL-6 receptor. By contrast, a so-called knock-in mouse prepared by the gene targeting method which involves replacing mouse genes with human genes has a structure where an mRNA transcribed from the coding sequence of a full-length human gene inserted in a target mouse gene contains a premature termination codon (PTC) of the inserted human gene far upstream of the termination codon of the mouse gene and also contains a mouse gene-derived exon-exon junction downstream of this PTC. When this structure is recognized by nonsense-mediated mRNA decay (NMD) system, the mRNA is degraded. For this reason, the gene expression level of interest is not obtained in many cases. As measures against this disadvantage, a poly A addition signal is added immediately downstream of the coding sequence, and the resulting construct is inserted to a mouse. As a result, the transcribed mRNA is structurally free from a target gene-derived exon-exon junction downstream of PTC and thus escapes NMD. An mRNA that does not undergo splicing out, however, is generally known to have a reduced expression level (Non Patent Literature 2). As mentioned above, it has been very difficult to prepare a non-human animal capable of expressing a foreign gene at a physiologically reasonable level while reducing its endogenous gene expression.

An hp7 sequence is a GC-rich nucleotide sequence and is known to form strong stem-loop when transcribed into an RNA. The functions of the hp7 sequence have previously been reported in two papers. One of the papers has reported that this sequence present 5' upstream of a translation initiation site causes a 40S ribosomal subunit to stall on the 5' side of a hairpin so that the translation is inhibited (Non Patent Literature 3). Another more recent paper discloses that the hp7 sequence present between PTC, which is subject to NMD, and an exon-exon junction suppresses NMD (Non Patent Literature 4), albeit with weak effects.

CITATION LIST

Non Patent Literature

Non Patent Literature 1: J. Exp. Med. 1995, Nov. 1; 182 (5): 1461-1468
Non Patent Literature 2: Proc. Natl. Acad. Sci. U.S.A. 85: 836-840
Non Patent Literature 3: Mol. Cell. Biol. 1989: 9: 5134-5142
Non Patent Literature 4: Nucleic Acid Research. 2012, doi: 10.1093/nar/gks344

SUMMARY OF INVENTION

Technical Problem

An object of the present invention is to provide a non-human animal capable of expressing a foreign gene at a physiologically reasonable level while lacking the expression of its endogenous gene (target gene), and also to provide a method for evaluating a compound using the animal. Another object of the present invention is to provide a method for producing an antibody having a desired activity by use of the evaluation method.

Solution to Problem

To attain the objects, the present inventors have attempted to prepare a mouse capable of expressing an inserted foreign gene at a physiologically reasonable level while deleting the expression of the endogenous target gene. As a result of conducting further diligent studies, the present inventors have found that a construct comprising an hp7 sequence and a poly A addition signal added downstream of the termination codon of a foreign gene can be inserted into a target gene of a mouse to thereby express the foreign gene in the mouse at a plasma concentration equivalent to that reported on humans.

Since the foreign gene inserted in this mouse contains the added poly A addition signal, the inserted foreign gene results in an mRNA that does not undergo splicing out. As described above, such an mRNA that does not undergo splicing out is known to have a reduced expression level (Non Patent Literature 2). Nonetheless, the present invention was able to circumvent this reduction in expression by use of the hp7 sequence.

The hp7 sequence inserted between PTC, which is subject to NMD, and an exon-exon junction is known to suppress NMD (Non Patent Literature 4). In the present invention, however, the obtained mRNA is free from the exon-exon junction downstream of PTC by virtue of the poly A addition signal present downstream of the hp7 sequence and thus escapes recognition by the NMD system.

As mentioned above, the present invention has gained the unexpected surprising finding that the foreign gene was successfully expressed at a physiologically reasonable level by use of the hp7 sequence under a mechanism other than the suppression of the NMD system.

The present inventors have also found that: a mouse in which a human interleukin-6 receptor gene is inserted in its interleukin-6 receptor gene manifests a symptom of a disease caused by human interleukin-6 or human interleukin-6 receptor by the overexpression of a human interleukin-6 gene in the mouse; and this symptom is ameliorated by the administration of a humanized neutralizing antibody. In this mouse that had received the humanized neutralizing antibody, the plasma concentration of a soluble human interleukin-6 receptor was elevated. This elevation is also commonly found in humans. As for a further advantage, the production of an endogenous mouse antibody recognizing the neutralizing antibody was suppressed in the mouse that had received the humanized neutralizing antibody. Specifically, the present inventors have also successfully prepared an excellent animal model that exhibits the pathological condition of a disease caused by human interleukin-6 or human interleukin-6 receptor. Use of this animal model enables a test substance to be conveniently examined for its therapeutic effect on the disease, pharmacokinetics, activity of removing a soluble human interleukin-6 receptor from blood, etc. Furthermore, use of such an evaluation system enables, for example, an antibody having a desired activity to be efficiently developed.

The present invention is based on these findings and specifically includes the following aspects:

[1] A non-human animal in which a DNA comprising an hp7 sequence-encoding DNA and a poly A addition signal-encoding DNA added on the 3' side of a DNA encoding an arbitrary foreign gene is inserted in the same reading frame as that of an arbitrary target gene present on the genome of the non-human animal.

[2] The non-human animal according to [1], wherein the foreign gene is a human interleukin-6 receptor gene.

[3] The non-human animal according to any one of [1] and [2], wherein the arbitrary target gene present on the genome of the non-human animal is an interleukin-6 receptor gene.

[4] The non-human animal according to any one of [2] and [3], wherein the non-human animal expresses a soluble human interleukin-6 receptor at a plasma concentration equivalent to that of the soluble interleukin-6 receptor in a healthy human.

[5] The non-human animal according to any one of [1] to [4], wherein the non-human animal is a rodent.

[6] The non-human animal according to any one of [1] to [5], wherein the non-human animal is a mouse.

[7] The non-human animal according to any one of [1] to [6], wherein human interleukin-6 is overexpressed.

[8] A method for evaluating the therapeutic effect of a test substance on a disease caused by human interleukin-6 or human interleukin-6 receptor, comprising the steps of:
(a) administering the test substance to a non-human animal according to [7]; and
(b) determining whether or not a symptom of the disease caused by human interleukin-6 or human interleukin-6 receptor has been suppressed in the non-human animal that has received the test substance.

[9] The method according to [8], wherein the disease caused by human interleukin-6 or human interleukin-6 receptor is Castleman's disease.

[10] A method for evaluating the pharmacokinetic properties of a test substance, comprising the steps of:
(a) administering the test substance to a non-human animal according to any one of [1] to [7]; and
(b) measuring the plasma concentration of the test substance in the non-human animal that has received the test substance.

[11] A method for evaluating a test substance for its activity of removing a soluble human interleukin-6 receptor from blood, comprising the steps of:
(a) administering the test substance to a non-human animal according to any one of [2] to [7]; and
(b) measuring the plasma concentration of the soluble human interleukin-6 receptor in the non-human animal that has received the test substance.

[12] The method according to any one of [7] to [11], wherein the test substance is an antibody against human interleukin-6 receptor.

[13] A method for producing an antibody against human interleukin-6 receptor having a therapeutic effect on a disease caused by human interleukin-6 or human interleukin-6 receptor, comprising the steps of:
(a) producing each antibody against human interleukin-6 receptor;
(b) administering the antibody to a non-human animal according to [7];
(c) determining whether or not a symptom of the disease caused by human interleukin-6 or human interleukin-6 receptor has been suppressed in the non-human animal that has received the antibody; and
(d) selecting an antibody that suppresses the symptom of the disease caused by human interleukin-6 or human interleukin-6 receptor.

[14] The method according to [13], wherein the disease caused by human interleukin-6 or human interleukin-6 receptor is Castleman's disease.

[15] A method for producing an antibody against human interleukin-6 receptor having desired pharmacokinetic properties, comprising the steps of:
(a) producing each antibody against human interleukin-6 receptor;
(b) administering the antibody to a non-human animal according to any one of [2] to [7];
(c) measuring the plasma concentration of the antibody in the non-human animal that has received the antibody; and
(d) selecting an antibody having the desired plasma concentration.

[16] A method for producing an antibody against human interleukin-6 receptor having an activity of removing a soluble human interleukin-6 receptor from blood, comprising the steps of:
(a) producing each antibody against human interleukin-6 receptor;
(b) administering the antibody to a non-human animal according to any one of [2] to [7];
(c) measuring the plasma concentration of the soluble human interleukin-6 receptor in the non-human animal that has received the antibody; and
(d) selecting an antibody that lowers the plasma concentration of the soluble human interleukin-6 receptor.

[17] The method for producing an antibody according to any one of [13] to [16], further comprising the step of (e) chimerizing or humanizing the selected antibody.

[18] A DNA for preparation of a non-human animal according to any of [1] to [7], the DNA comprising an hp7 sequence-encoding DNA and a poly A addition signal-encoding DNA added on the 3' side of a DNA encoding an arbitrary foreign gene.

[19] A knock-in vector for preparation of a non-human animal according to any of [1] to [7], the vector carrying a DNA according to [18].

[20] A transformed cell for preparation of a non-human animal according to any of [1] to [7], the transformed cell harboring a knock-in vector according to [19].

Advantageous Effects of Invention

The knock-in non-human animal of the present invention is capable of expressing a foreign gene at a physiologically reasonable level while suppressing the expression of its endogenous gene. Thus, use of the knock-in non-human animal of the present invention enables therapeutic agents highly specific for molecular targets, such as antibody drugs, to be properly evaluated.

BRIEF DESCRIPTION OF DRAWINGS

The patent or application file contains at least one drawing executed in color. Copies of this patent or patent application publication with color drawings will be provided by the Office upon request and payment of the necessary fee.

DESCRIPTION OF EMBODIMENTS

Figure 1A:
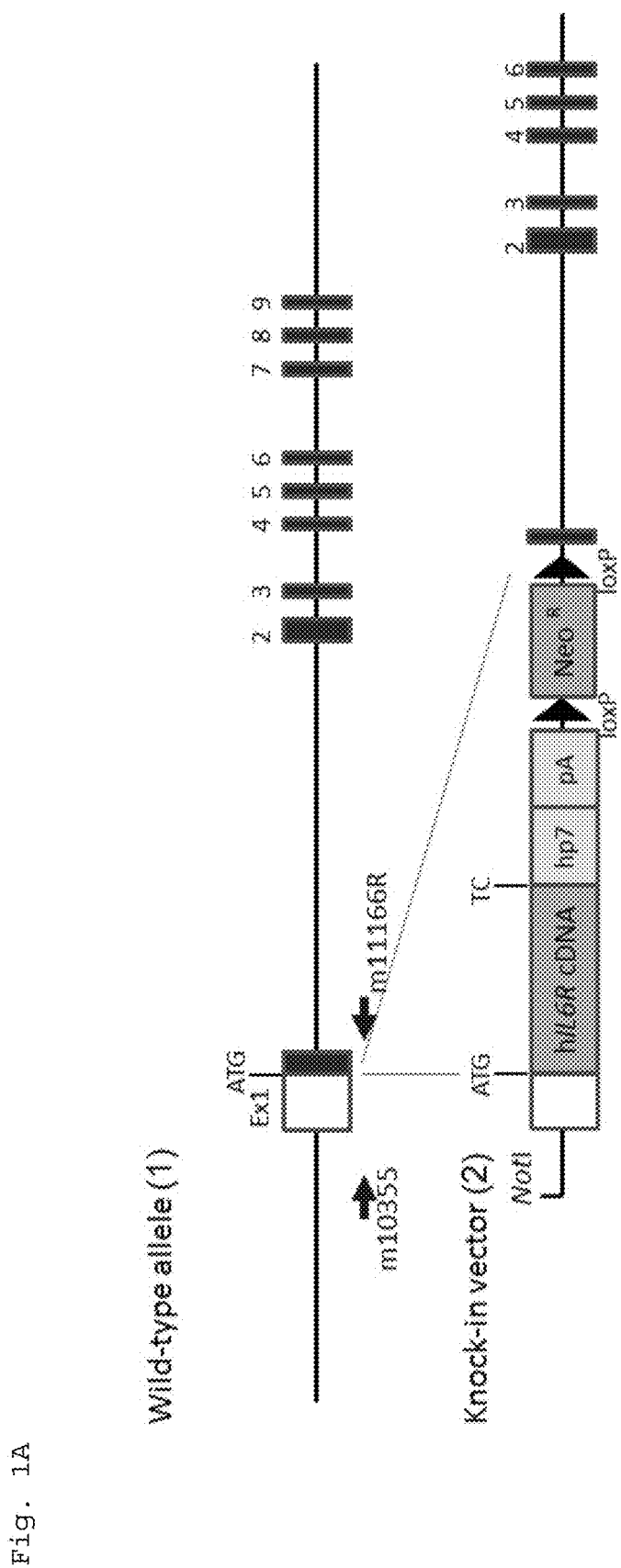
FIG. 1A is a diagram schematically showing the relationship between the genomic DNA structure (1) of a mouse interleukin-6 receptor (Il6ra) gene and a knock-in vector (2) to be inserted. The knock-in vector has a full-length human interleukin-6 receptor (hIL6R) cDNA, an hp7 sequence, a poly A addition signal, and a neomycin resistance gene.

The present invention provides a non-human animal in which a DNA comprising an hp7 sequence-encoding DNA and a poly A addition signal-encoding DNA added on the 3' side of a DNA encoding an arbitrary foreign gene is inserted in the same reading frame as that of an arbitrary target gene present on the genome of the non-human animal.

The "foreign gene" according to the present invention means a gene that is transferred to the non-human animal of the present invention. The foreign gene according to the present invention can be used without being limited by species of its origin. In the case of using the non-human animal of the present invention for the purpose of, for example, evaluating a therapeutic agent for a disease in humans, the foreign gene is preferably a human gene serving as a target molecule of the therapeutic agent for a disease. In the case of using the non-human animal of the present invention as a model of a disease caused by human interleukin-6 or human interleukin-6 receptor, the foreign gene is particularly preferably a human interleukin-6 receptor gene. The "human interleukin-6 receptor gene" of the present invention refers to a gene encoding a molecule that binds to human interleukin-6 and has the function of transducing signals into cells through its association with a signaling transducer gp130 on the cell membrane. Typically, a nucleotide sequence registered under GenBank No. # NM_000565 can be used in the present invention.

Alternatively, a selection marker gene such as a green fluorescence protein (GFP) gene, a reporter gene (e.g., a β-galactosidase gene), or a drug (neomycin or the like) resistance gene may be used as the foreign gene. Two or more genes may be used in combination as the foreign gene. In this case, a particular gene can be flanked by two loxP sequences and thereby removed by the action of Cre later. The foreign gene may also comprise an enhancer and the like added for regulation of the gene expression. The foreign gene is not particularly limited by its morphology and may be, for example, a cDNA or a genomic DNA.

In the present invention, an hp7 sequence-encoding DNA and a poly A addition signal-encoding DNA is added on the 3' side of a DNA encoding the foreign gene. In this context, the "hp7 sequence" refers to a nucleotide sequence GGGGCGCGTGGTGGCGGCTGCAGCCGCCAC-CACGCGCCCC (SEQ ID NO: 1). The "poly A addition signal" refers to a 6-bp nucleotide sequence containing AATAAA that resides in a noncoding region 3' downstream of the termination codon of the final exon of an eukaryotic gene and is necessary for adding 50 to 200 adenine nucleotides to the 3' end of the mRNA.

The "non-human animal" according to the present invention is not particularly limited, and a rodent such as a mouse, a rat, or a hamster, a non-human primate such as a monkey or a chimpanzee, a mammal such as a rabbit, sheep, cattle, or a pig, or any of other animals including birds, amphibians, reptiles, and fish can be used. The non-human animal is preferably a rodent, more preferably a mouse.

The "target gene" according to the present invention means a non-human animal gene to which the foreign gene is to be inserted. The "same reading frame" means a nucleotide sequence unit having base triplets that is read when an mRNA is translated into a protein. The phrase "inserted in the same reading frame" means that the foreign gene is inserted such that the start codon ATG of the foreign gene is consistent with the start codon ATG of the target gene. As a result, the inserted foreign gene is operably linked to a promoter of the target gene in the non-human animal and can be expressed in response to the activation of the promoter. For the insertion of the foreign gene, it is preferred that a sequence of a base length that is not a multiple of 3 should be deleted in a sequence following ATG of the target gene, from the viewpoint of eliminating the possibility of retranslating the disrupted target gene at the original reading frame. In the present invention, the foreign gene is preferably inserted in an exon containing the original translation initiation site of the target gene (i.e., the foreign gene undergoes homologous recombination only with the target exon of the target gene). A recognition sequence of recombinase, such as a loxP sequence, a Frt sequence, or a Rox sequence, may be further located 3' downstream of the poly A addition signal.

The non-human animal of the present invention in which the human interleukin-6 receptor gene is inserted as the foreign gene has a soluble human interleukin-6 receptor at a plasma concentration equivalent to that of the soluble interleukin-6 receptor in a healthy human. In this context, the concentration of the soluble interleukin-6 receptor in a healthy human refers to 15 to 70 ng/ml. The concentration of the soluble human interleukin receptor in the non-human animal can be measured by use of a method described in Examples.

In the case of using the non-human animal of the present invention as an animal model of, for example, a disease caused by human interleukin-6 or human interleukin-receptor, the non-human animal preferably further overexpresses human interleukin-6. The "overexpression" of human interleukin-6 means expression at a level exceeding the endogenous expression level of interleukin-6 in the non-human animal. A method for the overexpression of human interleukin-6 is not particularly limited, and, for example, the human interleukin-6 can be overexpressed by the transfer of the human interleukin-6 gene into the genome of the non-human animal using an expression vector containing a major histocompatibility antigen H-2Ld gene promoter. A promoter described in the literature (Miyazaki, J.-I. et al. (1986) Proc. Natl. Acad. Sci. USA. 83, 9537-9541) can be used as the major histocompatibility antigen H-2Ld gene promoter. The expression vector is not particularly limited as long as the vector can be used in genetic engineering. For example, a plasmid vector, a virus vector, a cosmid vector, a bacterial artificial chromosome (BAC), a yeast artificial chromosome (YAC), and any of other non-plasmid vectors can be used. Examples of the "disease caused by human interleukin-6 or human interleukin-6 receptor" include Castleman's disease, chronic rheumatoid arthritis, multiple myeloma, sepsis, mesangial nephritis, and cancer cachexia.

The present invention also provides a DNA for preparation of the non-human animal, a knock-in vector carrying the DNA, and a transformed cell harboring the knock-in vector.

The "DNA for preparation of the non-human animal" according to the present invention refers to a DNA comprising an hp7 sequence-encoding DNA and a poly A addition signal-encoding DNA added on the 3' side of a DNA encoding an arbitrary foreign gene.

The "knock-in vector carrying the DNA" of the present invention refers to a vector having the ability to insert the DNA for preparation of the non-human animal to the target gene region in a host through homologous recombination. In the vector, 5' arm (nucleotide sequence homologous to a nucleotide sequence 5' upstream of the target site) is positioned on the 5' side of the DNA for preparation of the non-human animal, while 3' arm (nucleotide sequence homologous to a nucleotide sequence 3' downstream of the target site) is positioned on the 3' side thereof. The knock-in vector according to the present invention is constructed so as to insert the DNA for preparation of the non-human animal to the same reading frame as that of the target gene in a host. Preferably, the knock-in vector allows the arbitrary foreign gene to be inserted in exon 1 of the target gene such that its translation initiation site is consistent with the translation initiation site of the exon 1. Specifically, a nucleotide sequence corresponding to a sequence upstream of the translation initiation site of the exon 1 of the target gene is preferably positioned on the 5' side of the translation initiation site of the arbitrary foreign gene in the knock-in vector.

Preferably, the knock-in vector of the present invention has the ability to replicate in host cells. Such a vector can be constructed, for example, by the insertion of the DNA for preparation of the non-human animal to a vector known in the art. Examples of the vector known in the art include plasmid vectors, bacterial artificial chromosome (BAC) vectors, yeast artificial chromosome (YAC) vectors, retrovirus vectors, and lentivirus vectors.

The "transformed cell harboring the knock-in vector" of the present invention refers to a cell to which the knock-in vector carrying the DNA for preparation of the non-human animal has been transferred. The host cell for transfer of the knock-in vector is a cell (or a cell population) of the non-human animal or a cell (or a cell population) that can be differentiated into the cell (population) of the non-human animal. Various cells can be used as such a host cell according to the purpose. Examples of the cells include: pluripotent stem cells such as ES cells and iPS cells; and germline stem cells capable of differentiating into germ cells, such as spermatogonial stem cells; and fertilized eggs. The knock-in vector can be transferred to the host cell by a method known in the art such as electroporation. The pluripotent stem cells are injected to early embryos by a method known in the art such as microinjection. The resulting embryos can be transplanted to a foster mother and developed to obtain a chimera animal. Also, progeny obtained by the breeding of this chimera animal can yield an individual having a homozygote of the knock-in allele. In the case of using the germline stem cells, the knock-in vector is transferred to the cells by a method known in the art such as electroporation. After target recombination, the cells are transplanted to the gonad of an animal and differentiated into germ cells. The knock-in animal can be produced by the mating of the animal or by use of the germ cells collected from the animal. For the method for producing genetically modified animals using the germline stem cells, see the literature (Kanatsu-Shinohara, M. et al. (2008) Biol. Reprod. 79, 1121-1128). In the case of using the fertilized eggs, the knock-in vector is injected, together with artificial nucleases (zinc finger nuclease (ZFN), transcription activator-like effector nucleases (TALEN), etc.), clustered regularly interspaced short palindromic repeat (CRISPR)/Cas9, or the like which binds to and cleaves a target sequence specific for a target region on the genome, into the fertilized eggs. The resulting fertilized eggs can be transplanted to a foster mother and developed to prepare a knock-in animal. The methods using ZFN and TALEN are described in the literature (Cui, X. et al. (2011) Nat. Biotechnol. 29, 64-67) and the literature (Li, T. et al. (2011) Nucleic Acids Res. 39, 6315-6325), respectively. The method using CRISPR/Cas9 is described in the literature (Yang, H. et al. (2013) Cell. in press). Alternatively, the knock-in vector may be injected to the testis or ovary of an animal, and its germ cells can be subjected directly to gene recombination by an approach such as electroporation, followed by mating to obtain an individual having a knock-in allele (Niu, Y. et al. (2008) J. Genet. Genomics. 35, 701-714).

The non-human animal of the present invention can be used in various evaluations of a test substance for its therapeutic effect on a disease, pharmacokinetics, activity of removing a soluble human interleukin-6 receptor from blood, etc. Hence, the present invention also provides such a method for evaluating a test substance using the non-human animal of the present invention.

Examples of the "test substance" used in the evaluation method of the present invention include, but are not particularly limited to, peptides, proteins, non-peptide compounds, synthetic compounds, fermentation products, and cell extracts. The test substance is preferably an antibody against human interleukin-6 receptor. Examples of the antibody include PM-1 antibodies (J. Immunol. 143: 2900-2906, 1989) and hPM-1 antibodies (International Publication No. WO 92/19759). The test substance can be administered to the non-human animal, for example, to the tail vein, subcutaneously, intraperitoneally, orally, transnasally, percutaneously, or transpulmonarily.

According to exemplary aspects, the test substance can be evaluated as described below. For example, the test substance can be evaluated for its therapeutic effect on a disease caused by human interleukin-6 or human interleukin-6 receptor by determining whether or not a symptom of the disease caused by human interleukin-6 or human interleukin-6 receptor has been suppressed in the non-human animal of the present invention that has received the test substance. Not only the non-human animal of the present invention (including its offsprings obtained by the mating with another non-human animal) but a biological material such as an organ, a tissue, a cell, or blood collected from the non-human animal can be used in the evaluation of whether or not a symptom of the disease has been suppressed. When the disease caused by human interleukin-6 or human interleukin-6 receptor is, for example, Castleman's disease, whether or not a symptom of the disease has been suppressed can be determined on the basis of improvement in the enlargement of the spleen and normalization of the increased weight of the spleen, etc.

Also, the test substance can be evaluated for its pharmacokinetic properties by measuring the plasma concentration of the test substance in the non-human animal of the present invention that has received the test substance. In this context, the "pharmacokinetic properties" mean properties such as the effective blood level, plasma half-life, and elimination rate of the test substance in the body of the animal. The approach of measuring the plasma concentration of the test substance is not particularly limited. When the test substance is a protein (including antibodies), examples of the approach include ELISA. When the test substance is a low-molecule-weight compound, examples thereof include liquid chromatography-mass spectrometry (LC-MS). For the methodology for evaluating the pharmacokinetic properties on the basis of the plasma concentration, see the literature (Igawa et al. (2010) Nat. Biotechnol. 28: 1203-1207).

Furthermore, the test substance can be evaluated for its activity of removing a soluble human interleukin-6 receptor from blood, by measuring the plasma concentration of the soluble human interleukin-6 receptor in the non-human animal of the present invention that has received the test substance. Examples of the approach of measuring the concentration of the soluble human interleukin-6 receptor include, but are not particularly limited to, ELISA.

This method can further involve measuring the plasma concentration of the test substance to thereby evaluate a dose of the test substance necessary for removing the soluble human interleukin-6 receptor from blood. The plasma concentration of the test substance can be measured by use of the method described above.

Use of the method for evaluating a test substance according to the present invention enables an antibody against human interleukin-6 receptor having a desired activity to be efficiently produced. Hence, the present invention also provides a method for producing such an antibody.

In the method for producing an antibody according to the present invention, each antibody against human interleukin-6 receptor is first produced.

Typical examples of methods for producing monoclonal antibodies include the method of Kohler and Milstein (Kohler & Milstein, Nature, 256: 495 (1975)). Antibody-producing cells for use in a cell fusion step in this method are, for example, spleen cells, lymph node cells, or peripheral blood leukocytes from an animal (e.g., a mouse, a rat, a hamster, a rabbit, a monkey, or a goat) immunized with the antigen human interleukin-6 receptor. Antibody-producing cells obtained by the action of the antigen in a medium on these cells or lymphocytes or the like isolated in advance from an unimmunized animal can also be used. Various cell lines known in the art can be used as myeloma cells. Hybridomas can be produced, for example, by the cell fusion between spleen cells obtained from a mouse immunized with the antigen and mouse myeloma cells and then screened to obtain a hybridoma producing the monoclonal antibody against human interleukin-6 receptor. The monoclonal antibody against human interleukin-6 receptor can be obtained by the culture of the hybridoma or from the ascitic fluid of a mammal given the hybridoma.

A DNA encoding the antibody may be cloned from the hybridoma or B cells or the like and incorporated into an appropriate vector, which can then be transferred to host cells (e.g., a mammalian cell line, $E.\ coli$, yeast cells, insect cells, or plant cells) to produce the antibody as a recombinant antibody (e.g., Antibody Production: Essential Techniques, 1997 WILEY; Monoclonal Antibodies, 2000 OXFORD UNIVERSITY PRESS; and Eur. J. Biochem. 192: 767-775 (1990)). A transgenic animal (e.g., cattle, a goat, sheep, or a pig) harboring the antibody gene may be prepared by the transgenic animal preparation technique, and the monoclonal antibody derived from the antibody gene can be obtained in large amounts from the milk of the transgenic animal.

Chimeric antibodies can be obtained, for example, by: immunizing a mouse with the antigen; cleaving genes of antigen-binding antibody variable domains (variable regions) from the mouse monoclonal antibody gene; linking the cleaved genes to genes of antibody constant domains (constant regions) derived from the human bone marrow; incorporating the resulting construct to expression vectors; and transferring the vectors to hosts for antibody production (e.g., Japanese Patent Laid-Open No. 7-194384, Japanese Patent No. 3238049, and U.S. Pat. Nos. 4,816,397, 4,816,567, and 5,807,715).

Humanized antibodies can be prepared by CDR grafting which involves transplanting gene sequences of antigen-binding sites (CDRs) of a non-human-derived antibody to a human antibody gene (see e.g., Japanese Patent Nos. 2912618, 2828340, and 3068507, European Patent Nos. 239400 and 125023, and International Publication Nos. WO 90/07861 and WO 96/02576).

A transgenic animal (e.g., a mouse) capable of producing human antibody repertoires by immunization can be used for the preparation of human antibodies (e.g., Nature, 362: 255-258 (1992); Intern. Rev. Immunol, 13: 65-93 (1995); J. Mol. Biol, 222: 581-597 (1991); Nature Genetics, 15: 146-156 (1997); Proc. Natl. Acad. Sci. USA, 97: 722-727 (2000); Japanese Patent Laid-Open No. 10-146194 and 10-155492, Japanese Patent No. 2938569, Japanese Patent Laid-Open No. 11-206387, and National Publication of International Patent Application No. 1996-509612 and 1999-505107).

An antibody against human interleukin-6 receptor having a therapeutic effect on a disease caused by human interleukin-6 or human interleukin-6 receptor can be obtained by: administering the antibody thus produced to the non-human animal of the present invention; determining whether or not a symptom of the disease caused by human interleukin-6 or human interleukin-6 receptor has been suppressed in the non-human animal that has received the antibody; and selecting an antibody that suppresses the symptom.

An antibody against human interleukin-6 receptor having desired disposition can be obtained by: measuring the plasma concentration of the antibody in the non-human animal that has received the produced antibody; and selecting an antibody having the desired plasma concentration.

An antibody against human interleukin-6 receptor having an activity of removing a soluble human interleukin-6 receptor from blood can be obtained by: measuring the plasma concentration of the soluble human interleukin-6 receptor in the non-human animal that has received the produced antibody; and selecting an antibody that lowers the plasma concentration of the soluble human interleukin-6 receptor.

When the antibody thus evaluated for its activity and selected is a mouse monoclonal antibody or the like, this antibody can be chimerized or humanized and then administered to a human to obtain an antibody with low antigenicity and, by extension, few adverse reactions.

EXAMPLES

Next, the present invention will be described more specifically with reference to Examples. However, the present invention is not intended to be limited by these Examples.

Example 1

Production of Human IL6R Gene Knock-in Mouse (1) Construction of Knock-in Vector An *E. coli* bacterial artificial chromosome (BAC) clone was used in which the genomic region of the mouse interleukin-6 gene (Il6ra) was cloned. A DNA fragment containing the coding sequence (GenBank # NM000565) of the human interleukin-6 receptor gene, an hp7 sequence, a poly A addition signal, a loxP sequence, a neomycin resistance (neo) gene cassette, and another loxP sequence connected in this order was inserted to the target region of the mouse Il6ra gene on the BAC through homologous recombination using Red/ET System (Gene Bridges GmbH). In this procedure, the DNA fragment was inserted in exon 1 of the mouse Il6ra gene on the BAC such that the translation initiation site of the human IL6R gene was consistent with a translation initiation site present in the exon 1, while only a 40-bp nucleotide sequence subsequent to the translation initiation site was deleted within the exon 1 of the mouse Il6ra gene. Since the drug resistance gene neo contains a pgk gene promoter, the neo gene is expressed in ES cells. The neo gene, however, may presumably suppress the expression of the hIL6R gene introduced upstream thereof. Thus, the neo gene was flanked by two loxP sequences (ATAACTTCG-TATAGCATACATTATACGAAGTTAT (SEQ ID NO: 2)) in order to remove the neo gene later. Under this mechanism, the neo gene flanked by the loxP sequences can be removed by recombination mediated by Cre. Subsequently, a restriction enzyme NotI recognition sequence (GCGGCCGC) was inserted, together with an ampicillin resistance gene, to a region 5' upstream of the mouse Il6ra gene on the BAC in order to linearize a knock-in vector.

(2) Transfer to ES Cell

The hIL6R knock-in vector thus obtained was transferred to ES cells (129SvEv mouse-derived) by electroporation. Drug resistance clones obtained after selective culture using G418 were screened for homologous recombinants by PCR. The knock-in vector was used after being linearized (60 μg), phenol/chloroform-extracted, then ethanol-precipitated, and dissolved in PBS.

The ES cells for use in screening were cultured in a 96-well plate and washed twice with 200 μl/well of a PBS solution. Then, a cell lysis buffer solution having the following composition (5 μl of 10×LA buffer II (for TAKARA LA Taq); 5 μl of 5% NP-40; 4 μl of proteinase K (Takara Bio Inc., 20 mg/ml); and 36 μl of distilled water) was added to each well. The mixture was treated at 55° C. for 2 hours and subsequently treated at 95° C. for 15 minutes for deactivation of the proteinase K to prepare a PCR sample.

A PCR reaction mixture contained 1 μl of the sample, 2.5 μl of 10×LA buffer II, 2.5 μl of 25 mM $MgCl_2$, 4 μl of dNTP (2.5 mM), 0.2 μl each of primers (each 50 μM), 0.25 μl of LA Taq (Takara Bio Inc.), and 14.35 μl of distilled water (25 μl in total). The PCR conditions consisted of preheating at 94° C. for 5 minutes, 35 amplification cycles each involving 98° C. for 10 seconds and 68° C. for 3.5 minutes, and additional heating at 68° C. for 7 minutes.

The primers used were as given below. A band of approximately 2.2 kb was amplified from the sample after the homologous recombination in the ES cells. The primer P6Ra1 was set in a mouse Il6ra genomic region upstream of the 5' homologous arm on the knock-in vector, while the primer hRLI6_11638R was set in the hIL6R cDNA (see FIG. 1). P6Ra1 (upstream) 5'-ACAGGGCCTTAGACT-CACAGC-3' (SEQ ID NO: 3); and hRLI6_11638R (downstream) 5'-AACTTGCTCCCGACACTACTGG-3' (SEQ ID NO: 4).

(3) Production of Knock-In Mouse

The homologous recombinant ES clones were detached by trypsin treatment and washed with an ES cell medium. Each female C57BL/6J (B6) mice superovulated by the intraperitoneal administration of 5 IU each of equine chorionic gonadotropin (eCG) and human chorionic gonadotropin (hCG) at an interval of 48 hours was mated with male mice of the same line thereas. When the day on which the vaginal plug of the female mice were confirmed was defined as day 0.5, the uterus and the oviducts were perfused on day 2.5 of pregnancy, and embryos at the 8-cell to morula stage was recovered. The recovered embryos were cultured overnight at 37° C., and 10 to 15 of the ES cells were injected to blastocysts developed from the embryos as host embryos. The embryos after the injection were transplanted into the uterus of a female recipient of ICR line on day 2.5 of pseudopregnancy. After 17 days, offsprings were obtained. As a result of determination based on the coat colors of the offsprings obtained by the injection of the ES cells to the blastocysts, chimera mice were obtained in which the recombinant ES cells (agouti coat color) coexisted with the host blastocyst-derived cells (black coat color). Each sexually matured male chimera mouse were mated with B6 female mice. The transmission of the knock-in allele to a next-generation mouse was confirmed by PCR using, as a template, a genomic DNA extracted from the tail of the next-generation mouse. This PCR was carried out by the aforementioned method used for the screening of the homologous recombinant ES cells. As a result, a signal of 2.2 kb was detected in individuals to confirm that the knock-in allele was transmitted to these individuals.

(4) Removal of Neo Gene

A Cre recombinase expression vector was microinjected to the pronuclei of the fertilized eggs obtained by the breeding of the individuals confirmed to contain the transmitted knock-in allele to thereby remove the neo gene cassette. Specifically, transiently expressed Cre induces the recombination between the two loxP sites positioned in the knock-in allele to remove the neo gene cassette. The fertilized eggs after the microinjection of the Cre expression vector were transplanted into the oviducts of female recipients of ICR line on day 0.5 of pseudopregnancy. After 19 days, offsprings were obtained. The removal of the neo gene cassette was confirmed by PCR using a genomic DNA extracted from the tail collected after weaning of the offsprings.

The composition of the PCR reaction solution was set to 1 µl of the sample, 12.5 µl of 2×GC buffer solution I, 4 µl of dNTP (2.5 mM), 0.25 µl each of primers (each 50 µM), 0.25 µl of LA Taq (Takara Bio Inc.), and 6.75 µl of distilled water (25 µl in total). The PCR conditions consisted of preheating at 94° C. for 4 minutes, 35 amplification cycles each involving 94° C. for 30 seconds, 62° C. for 30 seconds, and 72° C. for 3 minutes, and additional heating at 72° C. for 7 minutes.

Figure 1B:
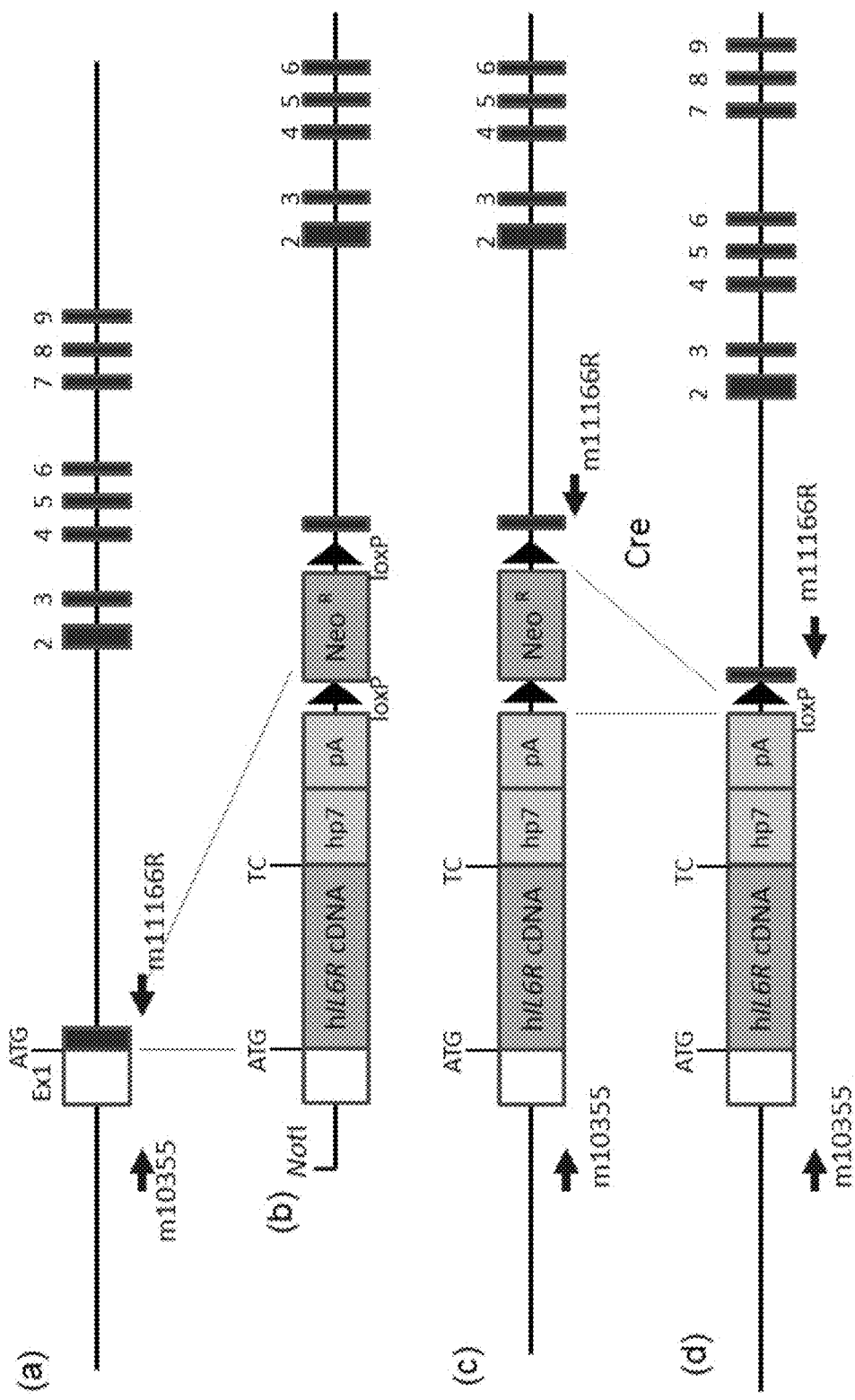
FIG. 1B is a diagram schematically showing a manner of formation of a genomic DNA (c) knocked-in by the homologous recombination of the genomic DNA (a) of the mouse interleukin-6 receptor gene with a knock-in vector (b). The diagram further shows a process of removing the neomycin resistance gene cassette by the action of recombinase Cre on the genomic DNA (c) to thereby complete a human interleukin-6 receptor gene knock-in allele (d). The arrows in the diagram represent the annealing positions of primers used for detecting the knock-in of the human interleukin-6 receptor gene.
Figure 2:
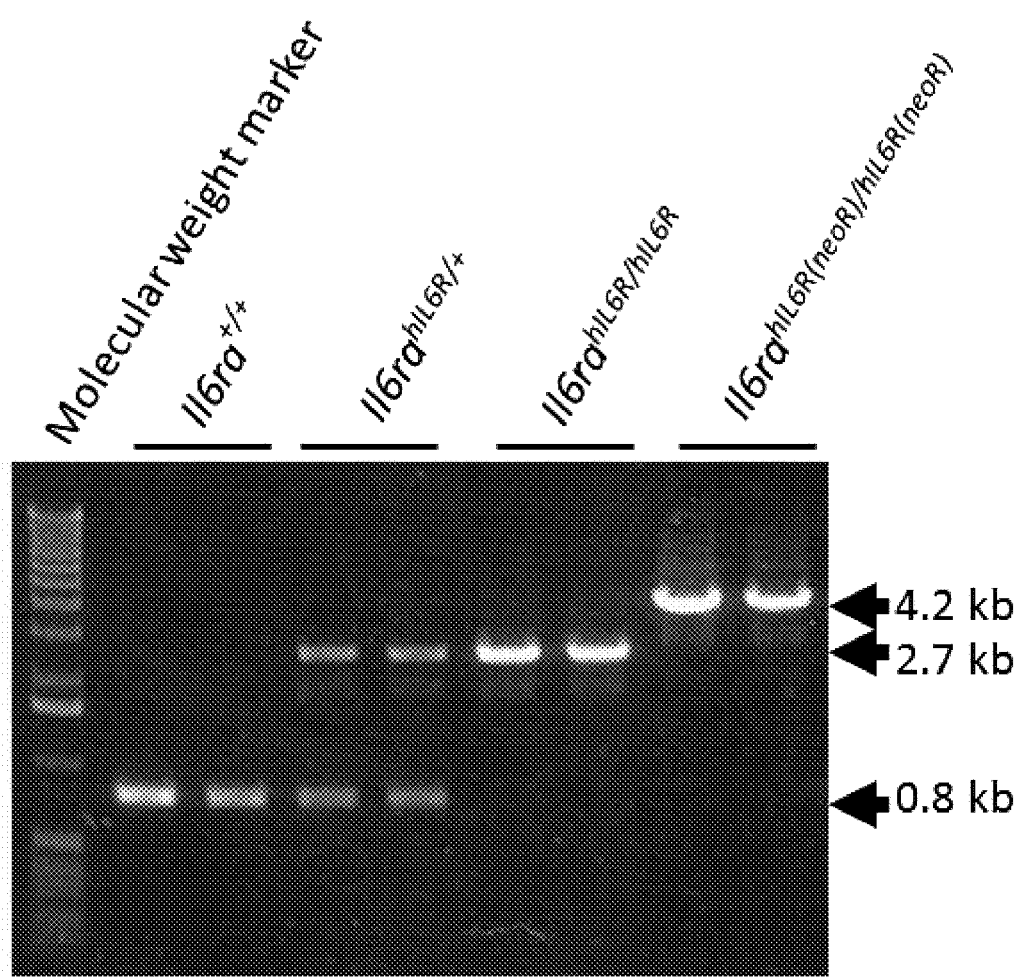
FIG. 2 shows a typical example of PCR by which each genotype obtained in a process of establishing the human interleukin-6 receptor gene knock-in mouse was analyzed.

The annealing positions of primers are shown in FIG. 1B. The primers used were mRLI6_10355 (5'-TCTGCAG-TAGCCTTCAAAGAGC-3' (SEQ ID NO: 5)) and mRLI6_11166R (5'-AACCAGACAGTGTCACATTCC-3' (SEQ ID NO: 6)). By this PCR reaction, the amplification product derived from the knock-in allele and the wild-type allele were detected as signals of 4.2 kb and 0.8 kb, respectively, in the samples of the individuals before the removal of the neo cassette, whereas the amplification product and the wild-type allele were detected as signals of approximately 2.7 kb and 0.8 kb, respectively, in the samples of the individuals after the removal of the neo cassette (FIG. 2).

(5) Establishment of Knock-In Mouse

Individuals having homozygous knock-in alleles were obtained by intercrossing of the mice confirmed lack of the neo gene cassette. The homozygote was confirmed by PCR. The PCR reaction was carried out in the same way as in the reaction system used for confirming the removal of the neo gene cassette. The signal of 2.7 kb derived from the knock-in allele is detected in the homozygote, whereas the signal of 0.8 kb derived from the wild-type allele is not detected therein. This was used as an index to confirm the homozygote (FIG. 2).

(6) Confirmation of Expression of Human IL6R and Mouse Il6ra

—Confirmation by RT-PCR Using Tissue RNA—

Figure 3:
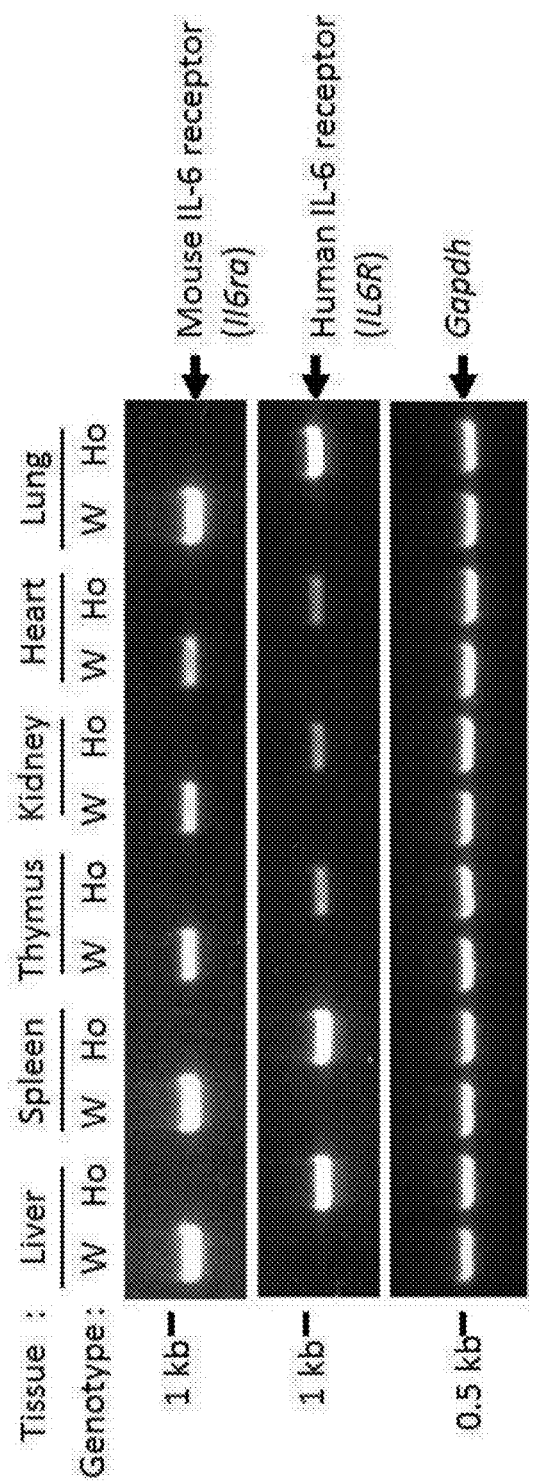
FIG. 3 is a diagram showing the interleukin-6 receptor gene expression properties of the human interleukin-6 receptor gene knock-in mouse and a wild-type mouse.

The expression of human IL6R and mouse Il6ra was analyzed by RT-PCR using tissue RNAs of the homozygous knock-in mouse and the wild-type mouse. The tissue RNAs were prepared from the liver, spleen, thymus, kidney, heart, and lung of each mouse. The tissue RNA (1 µg) of each origin was used as a template in reverse transcription reaction using SuperScript II First Strand cDNA Synthesis Kit (Invitrogen Corp.) and Oligo dT (20) primers to synthesize a cDNA. The synthesized cDNA was used as a template in PCR for the detection of human IL6R and mouse Il6ra. The human IL6R detection was carried out by the combined use of a forward primer 6RIK-s1 (5'-CCCGGCTGCG-GAGCCGCTCTGC-3' (SEQ ID NO: 7)) to be annealed to the 5' noncoding region upstream of the translation initiation site as the insertion site of the hIL6R gene in the knock-in allele and a human IL6R-specific reverse primer RLI6-a1 (5'-ACAGTGATGCTGGAGGTCCTT-3' (SEQ ID NO: 8)). On the other hand, the mouse Il6ra detection was carried out by the combined use of the aforementioned forward primer 6RIK-s1 and a mouse Il6ra-specific reverse primer 6RLIcA2 (5'-AGCAACACCGTGAACTCCTTTG-3' (SEQ ID NO: 9)). The composition of the PCR reaction solution was set to 1 µl of the sample, 12.5 µl of 2×GC buffer solution I, 4 µl of dNTP (2.5 mM), 0.25 µl each of primers (each 50 µM), 0.25 µl of LA Taq (Takara Bio Inc.), and 6.75 µl of distilled water (25 µl in total). The PCR conditions consisted of preheating at 94° C. for 2 minutes, 30 amplification cycles each involving 94° C. for 30 seconds, 62° C. for 30 seconds, and 72° C. for 1 minute, and additional heating at 72° C. for 5 minutes. Amplification products derived from the human IL6R and the mouse Il6ra, are detected at 880 bp and 846 bp, respectively. However, only the human IL6R was detected in each tissue of the homozygous hIL6R knock-in mouse, whereas the mouse Il6ra was not detected therein. The human IL6R was not detected in each tissue of the wild-type mouse, whereas only the mouse Il6ra was detected therein (FIG. 3). These results demonstrated that the knock-in vector underwent homologous recombination as designed to yield a mouse expressing human IL6R instead of mouse Il6ra.

—Measurement of Human IL6R Concentration in Plasma—

Figure 4:
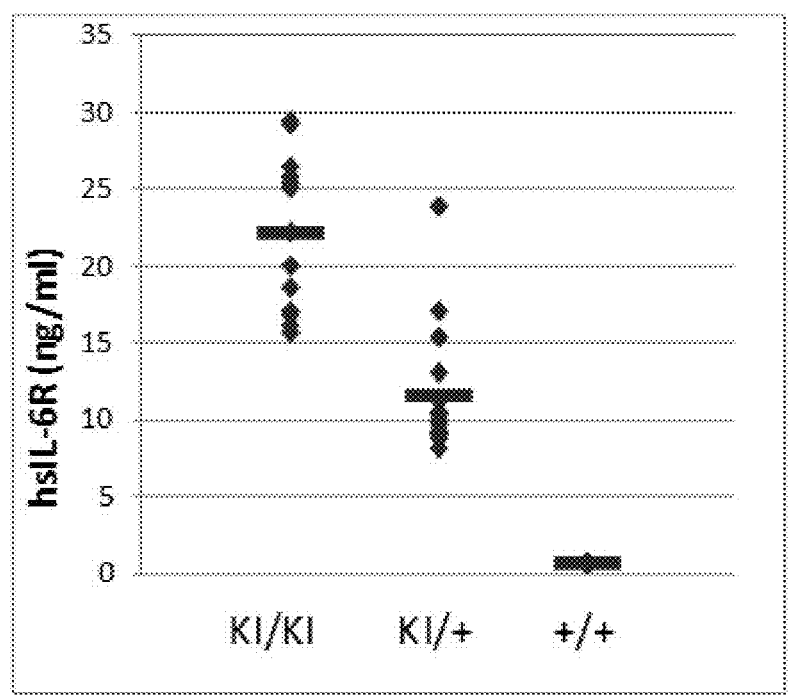
FIG. 4 is a graph showing the results of measuring soluble human interleukin-6 receptor (hsIL-6R) concentrations in the plasmas of homozygous and heterozygous human interleukin-6 receptor gene knock-in mice and a wild-type mouse. KI/KI, KI/+, and +/+ represent the homozygous knock-in mouse, the heterozygous knock-in mouse, and the wild-type mouse, respectively.

The abdomen was opened under anesthesia by isoflurane inhalation, and blood was collected from the abdominal vena cava. The soluble human IL6R concentration in plasma separated therefrom was measured using Quantikine Human IL-6 sR Immunoassay Kit (R&D Systems, Inc.). As a result, the plasma soluble hIL6R concentration was determined to be 22.1±5.0 ng/ml in the homozygous knock-in mouse and 11.5±4.1 ng/ml in the heterozygous knock-in mouse. No soluble hIL6R was detected in the plasma of the wild-type mouse (FIG. 4). The homozygous knock-in mouse had a plasma concentration equivalent to that reported on humans (Nishimoto N. et. al. (2008) Blood. 112: 3959-3969).

—Confirmation of Species-Specific Ligand Reactivity—

Figure 5:
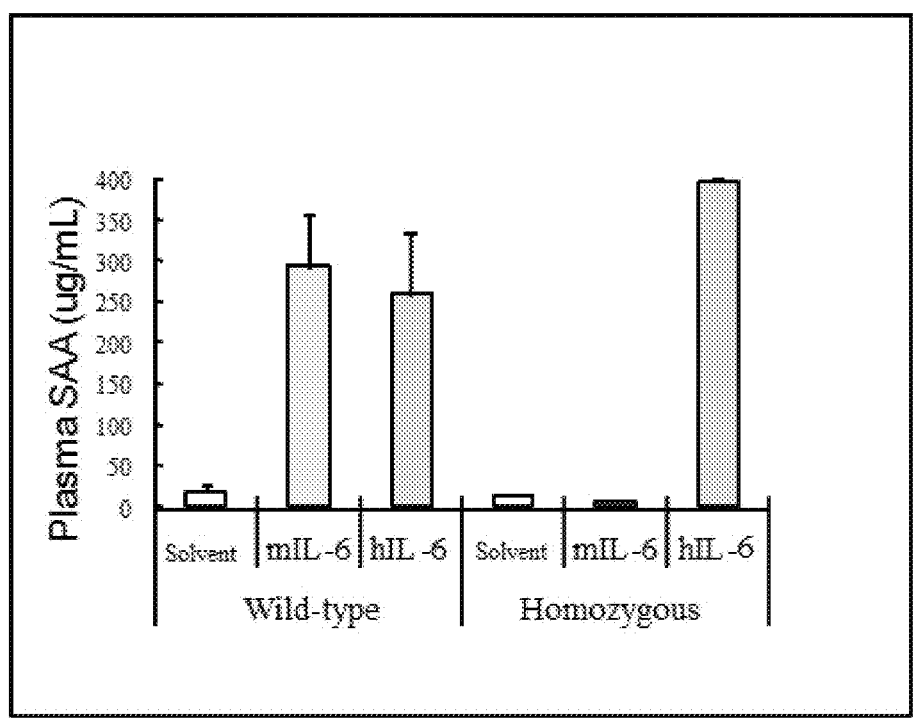
FIG. 5 is a graph showing the species-specific interleukin-6 (ligand) reactivity of a wild-type mouse and the homozygous human interleukin-6 receptor gene knock-in mouse.

Mouse IL6 or human IL6 was intraperitoneally administered at a dose of 4 μg/body weight kg to the homozygous knock-in mouse and the wild-type mouse. Blood was collected 6 hours thereafter, and the serum amyloid A (SAA) concentration in plasma was determined using SAA ELISA Kit (Invitrogen Corp.). The solvent used for each IL6 to be administered was a 0.5% solution of the mouse plasma supplemented with phosphate-buffered saline (PBS). An established control group received the solvent alone. As a result, the homozygous knock-in mouse exhibited an elevated plasma SAA level in response only to the human IL6, but was shown to have no reactivity with the mouse IL6 (FIG. 5). On the other hand, the wild-type mouse was shown to have an elevated plasma SAA level in response to both the human IL6 and the mouse IL6 (FIG. 5). It is known that the mouse Il6ra binds to both mouse IL6 and human IL6, whereas the human IL6R binds to human IL6 but does not bind to mouse IL6. The results of this experiment are consistent with this finding. These results demonstrated that the homozygous knock-in mouse, as designed, did not express mouse Il6ra and instead expressed functional human IL6R.

The hIL6R gene mRNA transcribed from the knock-in allele according to the present invention has a structure that does not undergo splicing out and thus escapes degradation by the NMD system. On the other hand, such a gene that does not undergo splicing out is known to have a reduced expression level. Nonetheless, the hIL6R knock-in mouse of the present invention was confirmed to have a plasma concentration of soluble hIL6R equivalent to that of the soluble hIL6R in healthy humans and to also produce SAA in adequate response to the administered human IL6. This indicates that the hp7 sequence inserted together with the poly A addition signal contributed to the stabilization of the hIL6R expression level supposed to be reduced due to the structure that does not undergo splicing out.

Example 2

Figure 6:
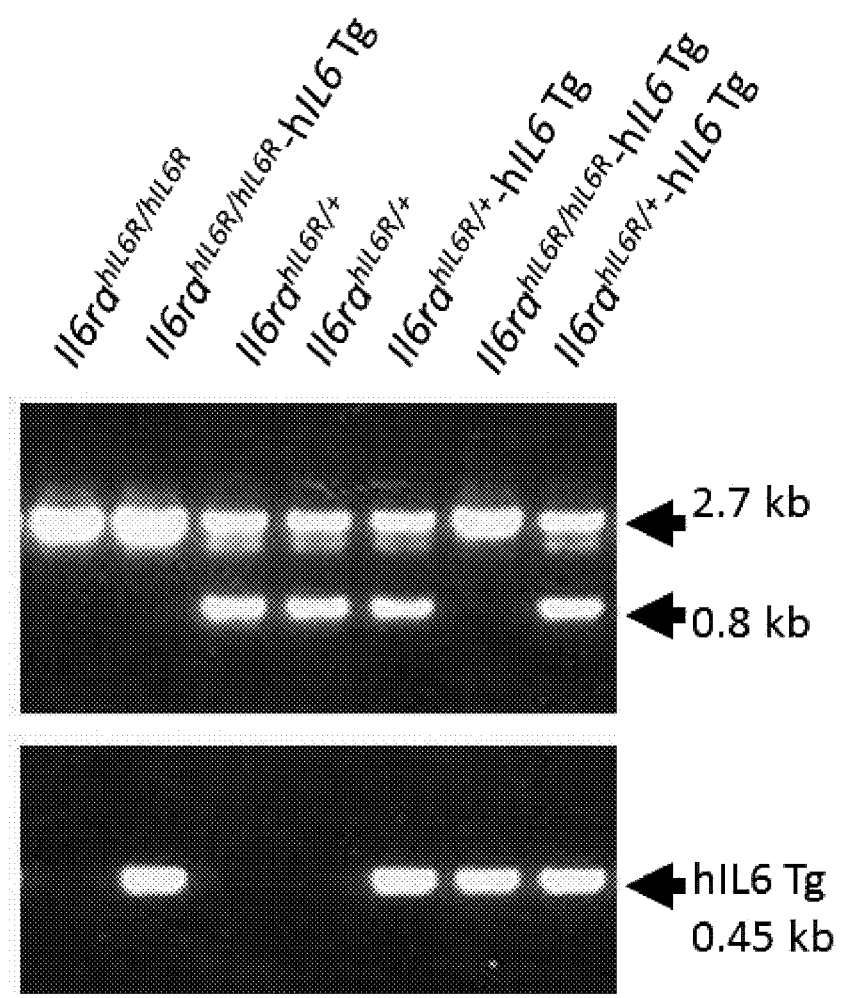
FIG. 6 shows a typical detection example of PCR genotype analysis in the establishment of a double transgenic mouse by the hybridization of the human interleukin-6 receptor gene knock-in mouse with a human interleukin-6 transgenic mouse.

Establishment and Evaluation of Humanized Mouse Model of Castleman's Disease (1) Establishment of Humanized Mouse Model of Castleman's Disease Double transgenic mice were produced by the mating of hIL6R knock-in mice with H-2Ld human IL6 transgenic mice (Cytokine. 2002, Dec. 21; 20 (6): 304-311). The genotype was analyzed by PCR using a genomic DNA extracted from a tissue of each individual to select individuals having the homozygous hIL6R knock-in allele and the hIL6 transgene. The hIL6R knock-in allele was detected using the aforementioned PCR reaction system. Specifically, the composition of the PCR reaction solution was set to 1 μl of the sample, 12.5 μl of 2×GC buffer solution I, 4 μl of dNTP (2.5 mM), 0.25 μl each of primers (each 50 μM), 0.25 μl of LA Taq (Takara Bio Inc.), and 6.75 μl of distilled water (25 μl in total). The PCR conditions consisted of preheating at 94° C. for 4 minutes, 35 amplification cycles each involving 94° C. for 30 seconds, 62° C. for 30 seconds, and 72° C. for 3 minutes, and additional heating at 72° C. for 7 minutes. The primers used were mRLI6_10355 (5'-TCT-GCAGTAGCCTTCAAAGAGC-3' (SEQ ID NO: 10)) and mRLI6_11166R (5'-AACCAGACAGTGTCACATTCC-3' (SEQ ID NO: 11)). By this PCR reaction, the knock-in allele and the wild-type allele were detected as signals of approximately 2.7 kb and 0.8 kb, respectively (FIG. 6). Further, the hIL6 transgene was detected by PCR. Specifically, the composition of the PCR reaction solution was set to 1 μl of the sample, 2.5 μl of 10×Ex buffer solution, 2 μl of dNTP (2.5 mM), 0.1 μl each of primers (each 50 μM), 0.25 μl of Ex Taq (Takara Bio Inc.), and 19.05 μl of distilled water (25 μl in total). The PCR conditions consisted of preheating at 94° C. for 4 minutes, 35 amplification cycles each involving 94° C. for 30 seconds, 65° C. for 30 seconds, and 72° C. for 30 seconds, and additional heating at 72° C. for 7 minutes. The primers used were a forward primer "5'-ACCTCTTCA-GAACGAATTGACAAA-3' (SEQ ID NO: 12))" and a reverse primer "5'-AGCTGCGCAGAATGAGATGAGT-TGT-3' (SEQ ID NO: 13)". The hIL6 transgene was detected at a chain length of 0.45 kb (FIG. 6). The mouse having the homozygous hIL6R knock-in allele and having the hIL6 transgene was confirmed to manifest Castleman's disease-like symptoms, i.e., the systemic swelling of lymph nodes and the enlargement of the spleen. The humanized mouse model of Castleman's disease thus established had the overexpression of human IL6 responsible for the pathological condition and produced its receptor IL6R in a humanized form.

(2) Study on Therapeutic Effect of hIL6R-Specific Neutralizing Antibody Administered to Humanized Mouse Model of Castleman's Disease The aforementioned humanized mouse model of Castleman's disease was used to study the possibility of pharmacological evaluation of a hIL6R-neutralizing antibody. A humanized anti-human IL6R monoclonal antibody (tocilizumab; hereinafter, referred to as TCZ) was administered at a dose of 2 mg/body into the tail vein of each humanized mouse model of Castleman's disease at the age of 4 weeks. From the next week, TCZ was subcutaneously administered thereto at a dose of 0.1, 0.25, or 0.5 mg/body with a frequency of twice/week for 4 weeks. For comparative controls, a rat anti-mouse Il6ra monoclonal antibody (MR16-1) was administered at a dose of 2 mg/body into the tail vein of each humanized mouse model of Castleman's disease at the age of 4 weeks. From the next week, MR16-1 was subcutaneously administered thereto at a dose of 0.1 mg/body twice a week for 4 weeks. An additional group received saline as a solvent. Further, the same antibody administration as above was also carried out to mice having wild-type Il6ra and the hIL6 transgene. Also, mice having the hIL6R knock-in mouse or the wild-type Il6ra but having no hIL6 transgene were used as control groups free from the pathological condition and received saline alone in the same protocol as above. All of these experimental groups used involved 5 individuals per group. Four days after the final administration, the abdomen was opened under anesthesia by isoflurane inhalation, and whole blood was collected. Then, each mouse was euthanized by bloodletting, and its spleen was collected. Heparinized plasma was collected from the collected blood and stored in a freezer of −80° C. The weight of the spleen was measured, and a portion thereof was cryopreserved at −80° C. for RNA preparation, while the remaining portion was dipped in a 10% neutral buffered formalin solution.

All of the hIL6R knock-in mice lacking the hIL6 transgene or the wild-type mice had a spleen weight of 0.08±0.01 g, even when given the solvent alone. The humanization of the IL6 receptor had no influence on the spleen weight. Next, the solvent-administered group of the hIL6 transgenic mice having the wild-type IL6 receptor had a spleen weight of 0.34±0.09 g, showing the enlargement of the spleen. On the other hand, the solvent-administered group of the hIL6R knock-in mice having the hIL6 transgene (i.e., the humanized mouse model of Castleman's disease) had a spleen weight of 0.26±0.03 g, showing the enlargement of the spleen in the mice expressing the humanized IL6 receptor, as in the mice expressing the mouse receptor.

Figure 7:
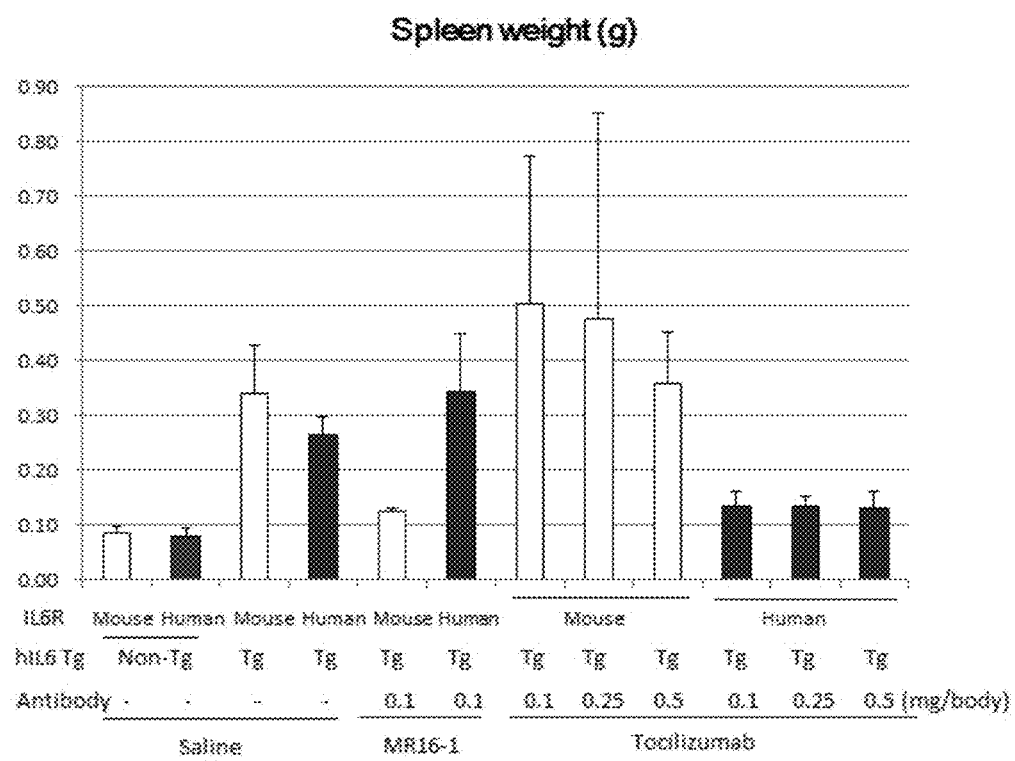
FIG. 7 is a graph showing the weight of autopsied spleens in an experiment of administration of each antibody (TCZ or MR16-1) to a humanized mouse model of Castleman's disease.

The administration of TCZ notably suppressed the enlargement of the spleen in the humanized mouse model of Castleman's disease (FIG. 7). Specifically, the groups given 0.1, 0.25, and 0.5 mg/body of TCZ had spleen weights (mean±standard deviation) of 0.14±0.03 g, 0.14±0.02 g, and 0.13±0.03 g, respectively, which were statistically significantly reduced compared with the spleen weight 0.26±0.03 g of the solvent-administered group. By contrast, the MR16-1-administered group had a spleen weight of 0.34 mg±0.11 g, which had no significant difference compared with the solvent-administered group. The solvent-administered group of the hIL6 transgenic mice having the wild-type Il6ra had a spleen weight of 0.34±0.09 g, showing the enlargement of the spleen, whereas the suppression of the enlargement of the spleen was not observed in the groups of these mice given any of the doses of TCZ (0.45±0.26 g). By contrast, the MR16-1-administered group of these mice was confirmed to have notable reduction in spleen weight to 0.12±0.01 g.

Figure 8:
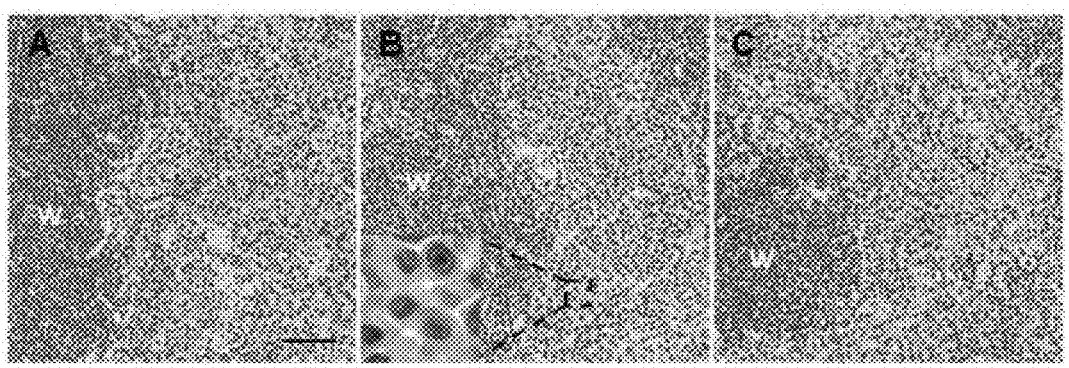
FIG. 8 is a histological picture showing a suppressive effect on increase in plasma cells in the spleen in the experiment of administration of TCZ to a humanized mouse model of Castleman's disease. A: hIL6R knock-in mouse, B: humanized mouse model of Castleman's disease that did not receive TCZ, and C: humanized mouse model of Castleman's disease that received TCZ.

The histopathological analysis of the spleens showed the increased number of plasma cells and the increased number of white pulps in the humanized mouse model of Castleman's disease, whereas the administration of TCZ improved all of these findings (FIG. 8, Table 1).

TABLE 1

Histopathological analysis of spleen in humanized mouse model of Castleman's disease receiving or not receiving tocilizumab

| | | Il6ra$^{hIL6R/hIL6R}$ | | |
| --- | --- | --- | --- | --- |
| Finding | Grade | No Tg Saline | hIL6 Tg Saline | hIL6 Tg TCZ* |
| Increase in plasma cells | — | 3/3 | 0/3 | 4/5 |
| | ± | 0/3 | 2/3 | 1/5 |
| | + | 0/3 | 1/3 | 0/5 |
| Increase in white pulps | — | 3/3 | 0/3 | 1/5 |
| | + | 0/3 | 0/3 | 4/5 |
| | ++ | 0/3 | 3/3 | 0/5 |

Grade: ±, very weak; +, weak; ++, moderate
The numerical values in the table represent the number of animals exhibiting the finding/the number of evaluated animals.
*Tocilizumab (TCZ) was administered.

Figure 9:
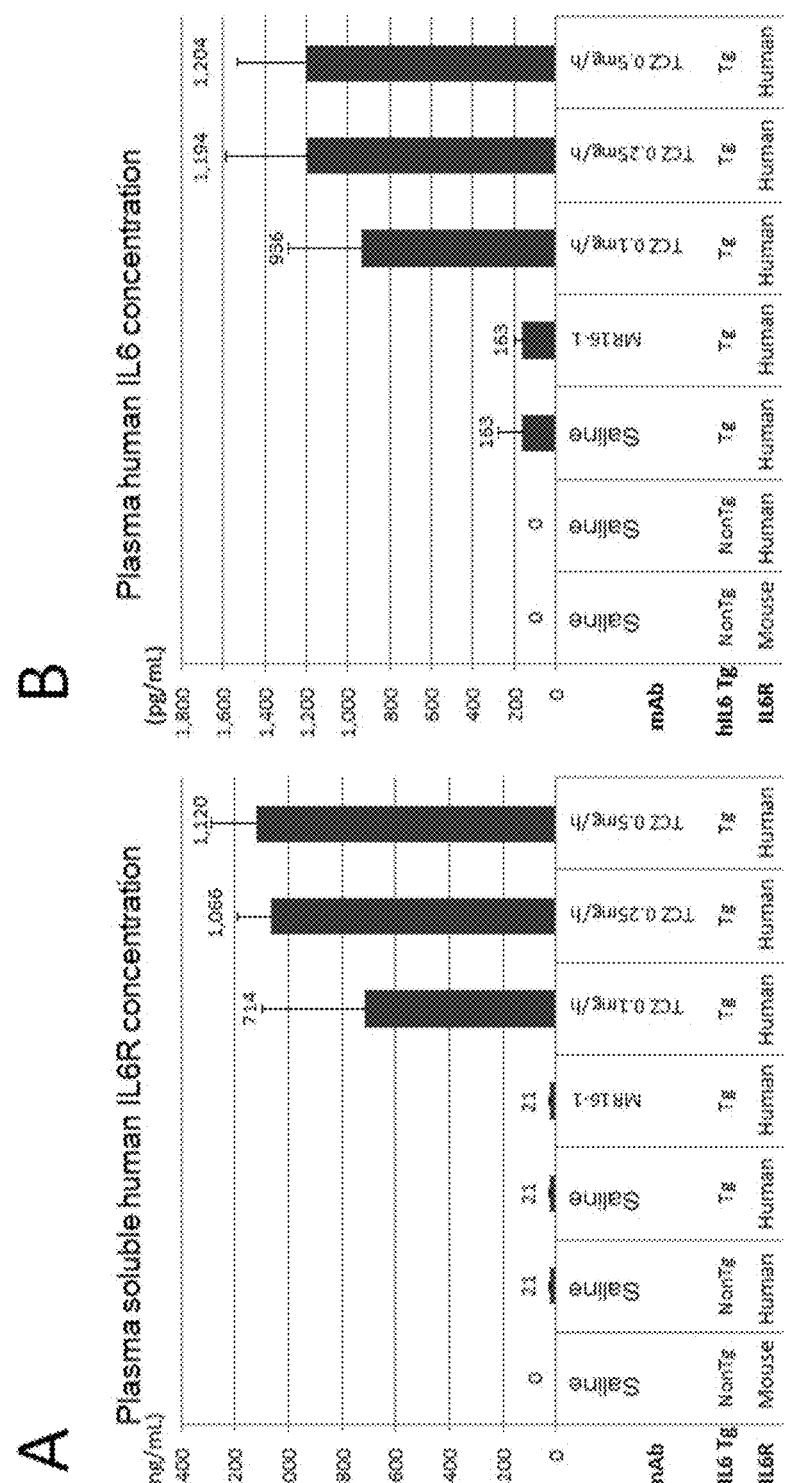
FIG. 9 is a diagram showing soluble human interleukin-6 receptor and human interleukin-6 concentrations in plasmas after autopsy in the experiment of administration of each antibody (TCZ or MR16-1) to a humanized mouse model of Castleman's disease.

The plasma soluble hIL6R concentration was measured using Quantikine Human IL-6 sR Immunoassay Kit (R&D Systems, Inc., DR600). The plasma hIL6 concentration was measured using Human IL-6 ELISA Kit (Invitrogen Corp., KHC0062). As a result, the administration of TCZ at any of the doses was confirmed to notably elevate the soluble hIL6R and hIL6 concentrations in the plasma of the humanized mouse model of Castleman's disease (FIG. 9). Specifically, the solvent-administered group had a plasma soluble hIL6R concentration of 21±7 ng/ml, whereas the groups given TCZ at the doses of 0.1, 0.25, and 0.5 mg/body twice a week showed notably elevated plasma concentrations of 713±387, 1066±126, and 1120±171 ng/ml, respectively. On the other hand, the MR16-1-administered group exhibited a plasma soluble hIL6R concentration of 21±2 ng/ml, which was similar to the concentration in the solvent-administered group. The solvent-administered group had a plasma hIL6 concentration of 163±112 pg/ml, whereas the groups given TCZ at the doses of 0.1, 0.25, and 0.5 mg/body twice a week showed notably elevated plasma concentrations of 936±350, 1194±394, and 1204±325 pg/ml, respectively. On the other hand, the MR16-1-administered group exhibited a plasma hIL6 concentration of 163±36 pg/ml, which was similar to the concentration in the solvent-administered group.

According to the report, the administration of TCZ to patients with Castleman's disease or chronic rheumatoid arthritis elevates their plasma soluble IL6R concentrations or IL6 concentrations (Blood. 2008 112: 3959-3969). Such elevation in the plasma concentration of the soluble IL6R is considered to be caused by prolonged clearance through the complexation of TCZ with the soluble IL6R in the blood. In addition, the plasma IL6 concentration seems to be elevated by reduction in the abundance ratio of IL6R uncomplexed with TCZ. In this experiment, the soluble hIL6R and hIL6 levels were also considered to be elevated in the TCZ-administered humanized mouse model of Castleman's disease under a similar mechanism as above. The hIL6R knock-in mouse and the humanized mouse model of Castleman's disease had a plasma hIL6R concentration equivalent to that reported on patients with Castleman's disease or chronic rheumatoid before the TCZ administration and as such, can be expected to serve as mouse models effective for predicting changes in the plasma level of the antigen in human patients. Particularly, an antibody can probably be evaluated for its function of removing hIL6R from blood, by monitoring changes in the plasma level of the soluble hIL6R after administration of the antibody. In addition, the mouse is a small laboratory animal and as such, can minimize the necessary amount of the test antibody for comparative study.

—Evaluation of Plasma Anti-TCZ Antibody Titer—

Figure 10:
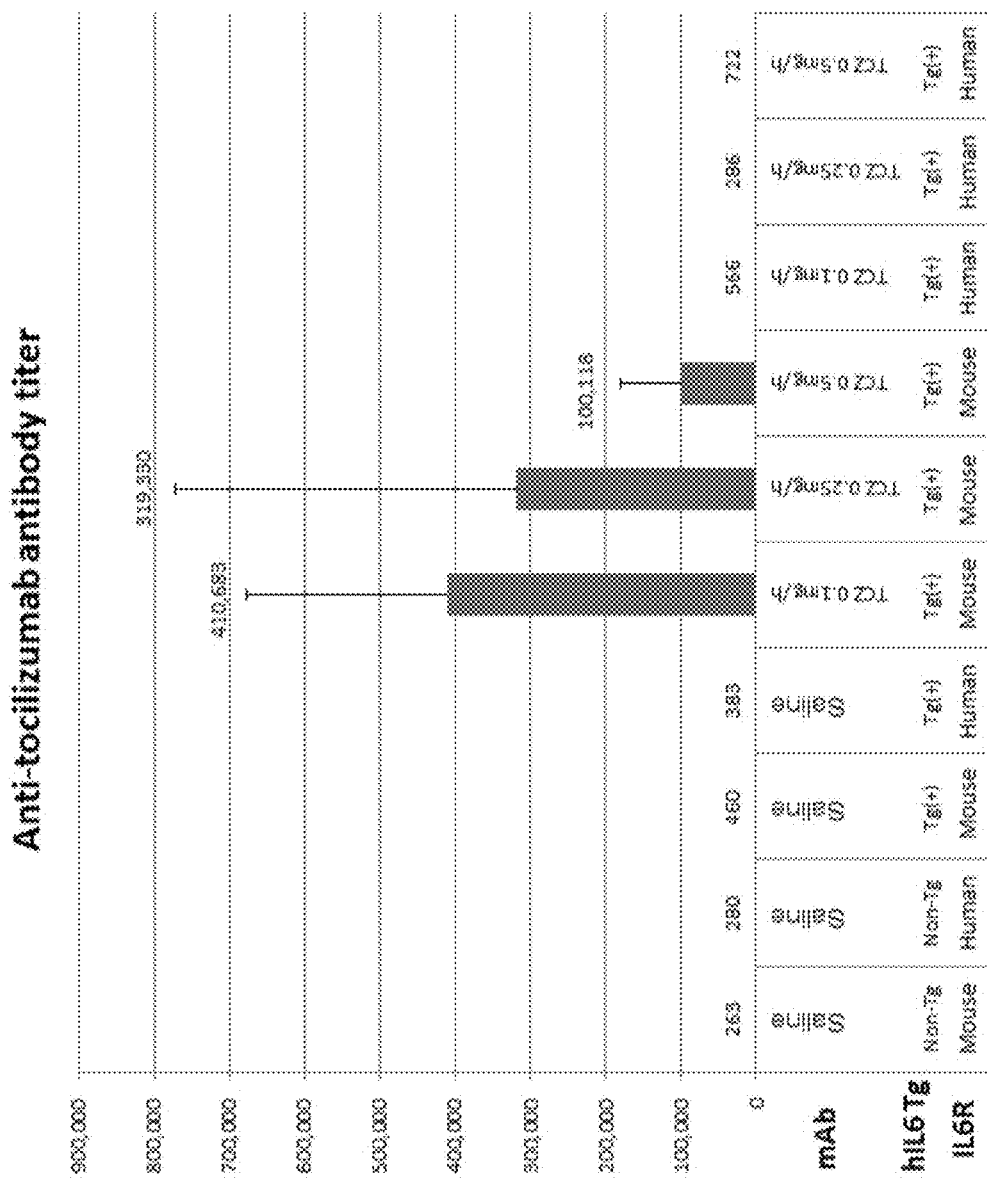
FIG. 10 is a diagram showing anti-TCZ antibody titers in plasmas after autopsy in the experiment of administration of each antibody (TCZ or R16-1) to a humanized mouse model of Castleman's disease.

The anti-TCZ antibody titer was measured using plasma samples obtained by autopsy. Specifically, each plasma sample was mixed with a biotinylated TCZ antibody and a SULFO-TAG-labeled TCZ antibody and incubated overnight, followed by addition to an MSD-streptavidin plate. Subsequently, an ECL (enhanced chemiluminescence) substrate was added to the plate, and the intensity of chemiluminescence was measured. As a result, the hIL6 transgenic mice having the wild-type interleukin-6 receptor exhibited an exceedingly high anti-TCZ antibody titer by the administration of TCZ at any dose, whereas anti-TCZ antibody production was exceedingly suppressed in the humanized mouse model of Castleman's disease by the administration of TCZ at any dose (FIG. 10). This demonstrated that the anti-TCZ antibody production is suppressed by the blockade of signals from the interleukin-6 by the action of TCZ.

Example 3

Figure 11A:
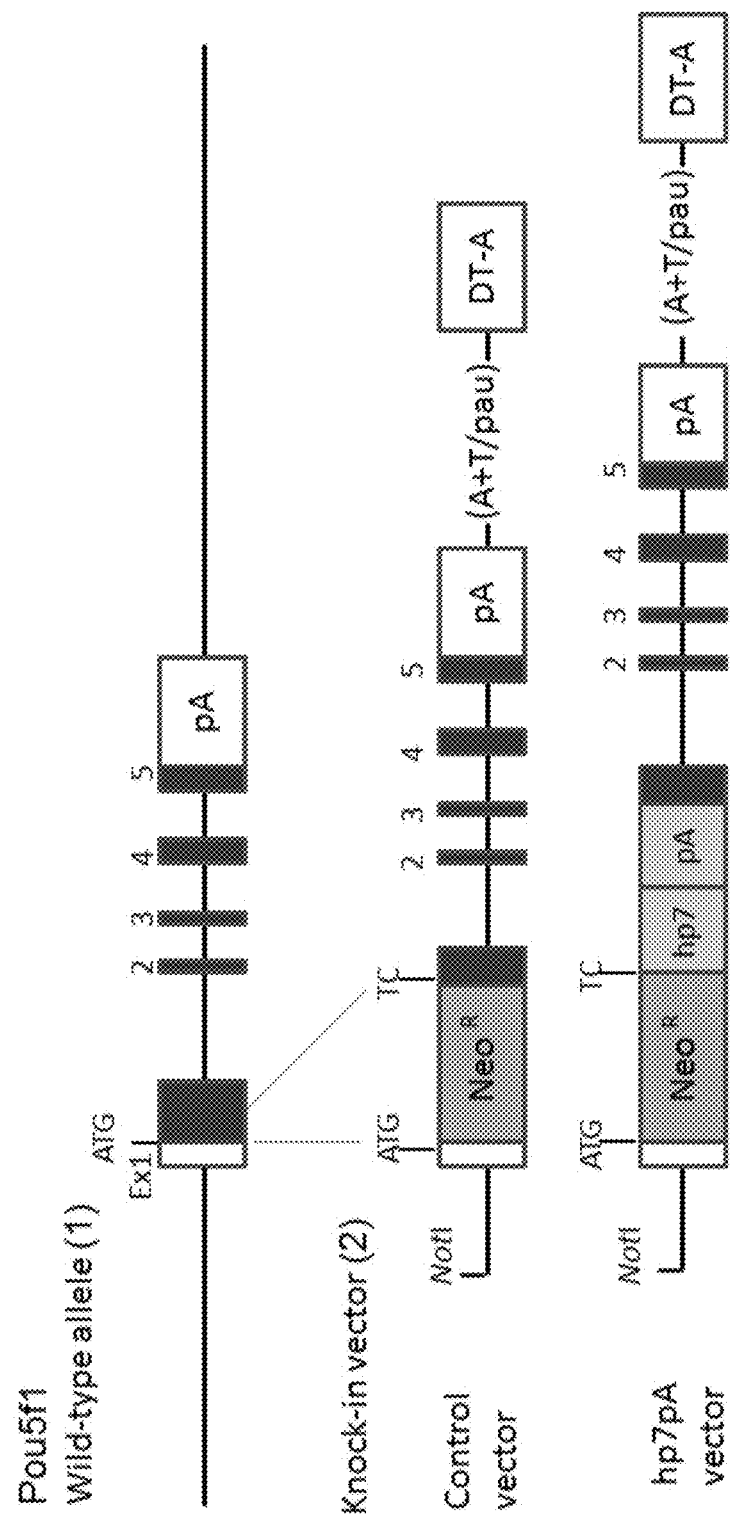
FIG. 11A is a diagram schematically showing the relationship between the genomic DNA structure (1) of a mouse Pou5f1 gene and each knock-in vector (2) to be inserted. Of the knock-in vectors, the control vector has a neomycin resistance (neo) gene cDNA, and the hp7 pA vector has a neomycin resistance (neo) gene cDNA, an hp7 sequence, and a poly A addition signal. In these knock-in vectors, the neomycin resistance (neo) gene cDNA was inserted in exon 1 of the mouse Pou5f1 gene such that its translation initiation site was consistent with the translation initiation site of the exon 1.

Knock-in of Neomycin Resistance Gene to Mouse Pou5f1 Locus (1) Construction of Knock-In Vector The neomycin resistance (neo) gene was inserted in exon 1 of the mouse Pou5f1 gene such that the translation initiation site of the neomycin resistance (neo) gene was consistent with a translation initiation site present in the exon 1, while only a 107-bp nucleotide sequence subsequent to the translation initiation site was deleted within the exon 1 of the mouse Pou5f1 gene to construct a knock-in vector. By this procedure, two types of vectors were constructed: an hp7pA vector containing an hp7 sequence and a poly A addition signal connected immediately downstream of the termination codon of the neo gene; and a control vector to utilize its endogenous poly A addition signal without insertion both of the hp7 sequence and the poly A addition signal. A structure connected to a genomic DNA region up to 1.7 kb upstream of the aforementioned translation initiation site of the Pou5f1 gene and a genomic DNA region of approximately 5 kb subsequent to the deleted region of the exon 1 was formed as the homologous arms of the knock-in vector. The resulting construct was inserted to a vector pMC1DTA (A+T/pau) (Yagi T. et. al. (1993) Anal Biochem. 214: 77-86). The knock-in vector contained a restriction enzyme NotI recognition sequence (GCGGCCGC) at the 5' end of the upstream homologous arm and can therefore be linearized with NotI. The structure of each vector is shown in FIG. 11A.

(2) Transfer to ES Cell

Each knock-in vector thus obtained was transferred to ES cells (C57BL/6N mouse-derived) by electroporation, followed by selective culture using G418. The knock-in vector was used after being linearized with NotI, phenol/chloroform-extracted, then ethanol-precipitated, and dissolved in PBS. For the electroporation, concentration adjustment was performed such that 20 µg of the knock-in vector was transferred to 2×10⁷ ES cells. The electroporation of the ES cells was carried out twice for each vector in order to confirm reproducibility. The ES cells thus electroporated were seeded. After 24 hours, a medium containing 300 µg/mL of G418 was added thereto for selective culture.

(3) PCR Screening for Detection of Homologous Recombinant Clone

ES cell colonies derived from the hp7pA vector were picked up and studied for the efficiency of homologous recombination. Specifically, the ES cells were cultured in a 96-well plate and washed twice with 200 µl/well of a PBS solution. Then, a cell lysis buffer solution having the following composition (5 µl of 10×LA buffer solution II (for TAKARA LA Taq); 5 µl of 5% NP-40; 4 µl of proteinase K (Takara Bio Inc., 20 mg/ml); and 36 µl of distilled water) was added to each well. The mixture was treated at 55° C. for 2 hours and subsequently treated at 95° C. for 15 minutes for deactivation of the proteinase K to prepare a PCR sample.

A PCR reaction mixture contained 1 µl of the sample, 2.5 µl of 10×LA buffer II, 2.5 µl of 25 mM MgCl₂, 4 µl of dNTP (2.5 mM), 0.1 µl each of primers (each 50 µM), 0.25 µl of LA Taq (Takara Bio Inc.), and 14.55 µl of distilled water (25 µl in total). The PCR conditions consisted of preheating at 94° C. for 2 minutes, 35 amplification cycles each involving 98° C. for 10 seconds, 60° C. for 15 seconds, and subsequently 68° C. for 3 minutes, and additional heating at 68° C. for 5 minutes.

Figure 11B:
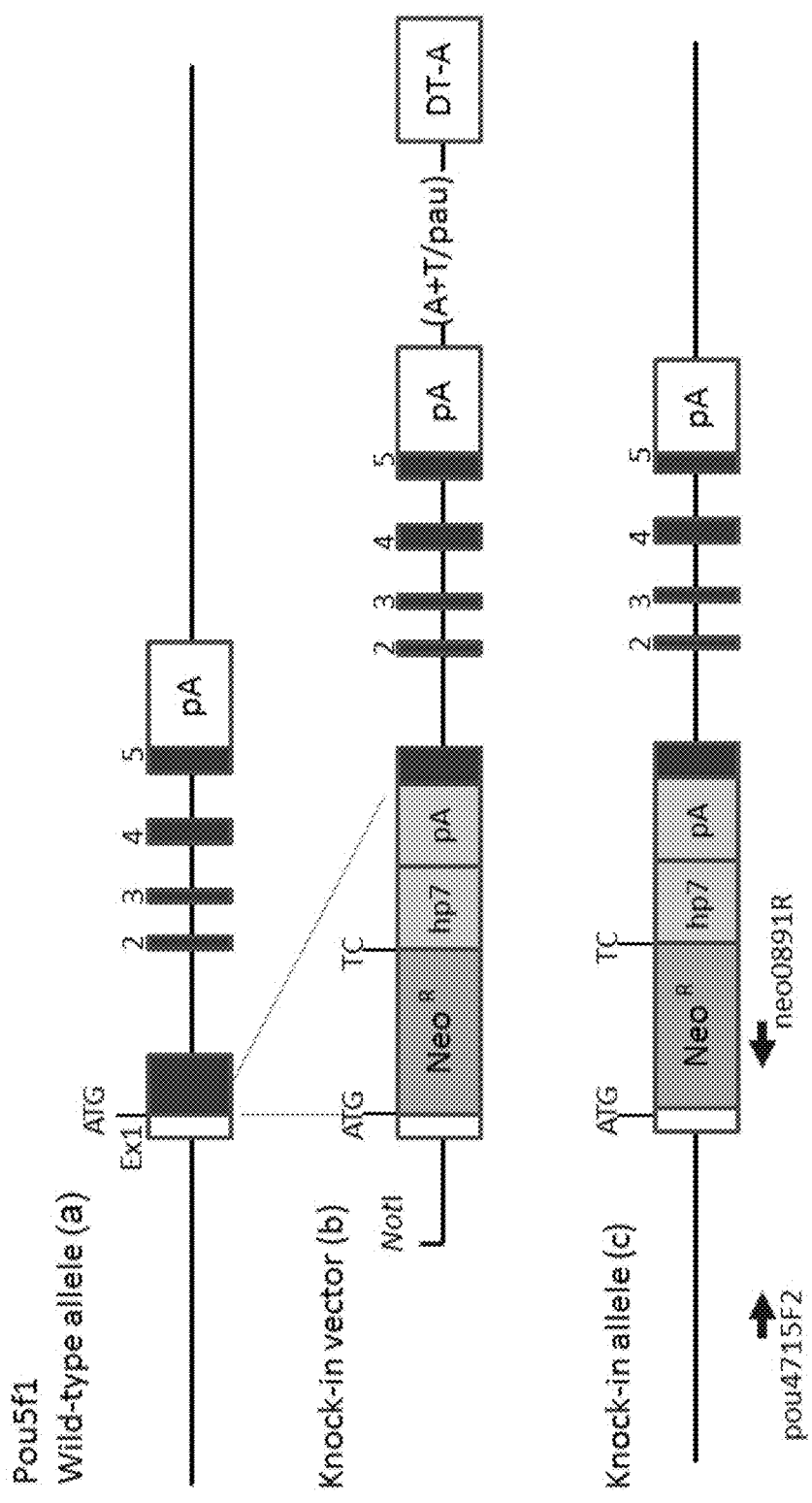
FIG. 11B is a diagram schematically showing a manner of formation of a genomic DNA (c) knocked-in by the homologous recombination of the genomic DNA (a) of the mouse Pou5f1 gene with a knock-in vector (b). The arrows in the diagram represent the annealing positions of primers used for detecting the knock-in of the neo gene.

The primers used were as given below. A band of approximately 2.2 kb was amplified from the sample after the homologous recombination in the ES cells. The primer Pou4175F2 was set in a mouse Pou5f1 genomic region upstream of the 5' homologous arm on the knock-in vector, while the primer neo8916R was set in the neo gene cDNA (see FIG. 11B). Pou4175F2 (upstream) 5'-AAGTCGCTGC-CTTTATTTAGGTCTTCCAACTAACC-3' (SEQ ID NO: 14); and neo0891R (downstream) 5'-TTCAGT-GACAACGTCGAGCACAGCTGC-3' (SEQ ID NO: 15).

Table 2 summarizes the number of ES cell clones rendered G418-resistant by the transfer of the neo gene knock-in vector to the Pou5f1 gene region, the number of homologous recombinant clones after this transfer, and the efficiency of the homologous recombination.

TABLE 2

Performance of transfer of neo gene knock-in vector to Pou5f1 gene region

| Vector | Electroporation | | | The number of clones | | Homologous recombinant/ |
|---|---|---|---|---|---|---|
| | | The number of ES cells | Vector (µg) | G418-resistant clone | Homologous recombinant | G418-resistant clone (%) |
| Control vector | 1 | 0.6 × 10⁷ | 20 | 0 | — | — |
| | 2 | 0.6 × 10⁷ | 20 | 0 | — | — |
| | Total | | | 0 | — | — |
| hp7pA vector | 1 | 0.6 × 10⁷ | 20 | 82 | 34 | 41% |
| | 2 | 0.6 × 10⁷ | 20 | 85 | 30 | 35% |
| | Total | | | 167 | 64 | 38% |

First, the growth situation of the ES cell colonies carrying the control vector were observed 10 days after the seeding. As a result, normally grown ES cell colonies were not obtained. On the other hand, normally grown ES cell colonies were observed by the transfer of the hp7pA vector.

Both of the knock-in vectors had totally the same chain lengths of the homologous arms and are therefore thought to have the equivalent efficiencies of insertion of the neo gene to the target region by homologous recombination. In the case of the control vector, however, it appeared that the neo gene was expressed in an amount insufficient for conferring G418 resistance even if the neo gene was inserted to the region as expected.

The transferred hp7pA vector yielded 167 G418-resistant clones derived from the 2 electroporation runs. These G418-resistant clones were analyzed using the aforementioned PCR system. As a result, homologous recombinant neo gene knock-in clones were 64 out of the 167 clones (38%). In the case of the transferred hp7pA vector, the neo gene was inserted to the target region of the endogenous Pou5f1 gene through homologous recombination so as to attain the consistency of their translation initiation sites. Probably, the neo gene was expressed by the control of the Pou5f1 gene promoter activated in the ES cells to confer G418 resistance to the clones. In the clones found to be negative as a result of PCR, it appeared that the neo gene was transferred downstream of some gene promoter that was located at a random position on the chromosome and activated in the ES cells, rather than the target region. In other words, these negative clones were judged as being G418-resistant, because the neo gene was expressed by the activity of a promoter present in the neighborhood of the insertion site. From these results, it was assumed that the sufficient expression level of the neo gene was obtained by virtue of the presence of the hp7 sequence and the poly A addition signal, regardless of whether the gene was inserted to the target region or inserted to a random position.

In this experiment, the neo gene was inserted to the Pou5f1 gene such that their translation initiation sites were consistent with each other, while the region to be deleted in the target gene was minimized. The mRNA transcribed from the gene allele modified with the control vector has a structure that contains a premature termination codon (PTC) of the inserted neo gene far upstream of the termination codon of the Pou5f1 gene and also contains a Pou5f1 gene-derived exon-exon junction downstream of this PTC. When this structure is recognized by nonsense-mediated mRNA decay (NMD) system, the mRNA is degraded. For this reason, the neo gene was presumably expressed at a level insufficient for conferring G418 resistance. If only the poly A addition signal is added immediately downstream of the neo gene, an mRNA transcribed from the resulting construct is structurally free from a target gene-derived exon-exon junction downstream of PTC and thus escapes NMD. The mRNA having such a structure that does not undergo splicing out, however, is highly likely to have a reduced expression level (Non Patent Literature 2). On the other hand, if the hp7 sequence, which forms strong stem-loop, is inserted immediately downstream of the neo gene, the possibility is expected that NMD is suppressed (Non Patent Literature 4). Unfortunately, the hp7 sequence itself produces a weak NMD-suppressing effect as predicted from the description of Non Patent Literature 4 and cannot be expected to stabilize the gene expression.

In consideration of these factors, the experiment results obtained this time strongly suggest that in the case of transferring a foreign gene to a target gene region via the knock-in vector, the hp7 sequence and the poly A addition signal both inserted immediately downstream of the foreign gene are likely to stabilize the expression of the knocked-in foreign gene. Even if any of the control vector and the hp7pA vector is used, the neo gene may be inserted to the target region through homologous recombination. In such a case, presumably, these vectors do not differ in the control of transcription by a promoter, because the vectors have totally the same 5' upstream regions. Accordingly, it is strongly suggested that the difference in the expression level of the neo gene is attributed to the stabilization of an mRNA by the simultaneous insertion of the hp7 sequence and the poly A addition signal downstream of the termination codon in the mRNA structure. In addition, the structure of this vector carrying the poly A addition signal thus inserted causes no NMD, indicating that the action of the hp7 sequence is based on a newly found function different from the known NMD-suppressing effect.

INDUSTRIAL APPLICABILITY

The present invention provides a non-human animal capable of expressing a foreign gene at a physiologically reasonable level while lacking the expression of its endogenous gene (target gene), and also provides a method for evaluating a compound using the animal. Thus, the present invention can be used particularly in the development of therapeutic agents highly specific for molecular targets.

Free Text for Sequence Listing
   SEQ ID NO: 1
<223> hp7 sequence
   SEQ ID NOs: 3 to 15
<223> sequences of artificially synthesized primers

The invention claimed is:

1. A rodent in which a DNA comprising an hp7 sequence-encoding DNA and a poly A addition signal-encoding DNA added on the 3' side of a DNA encoding a foreign gene is inserted in the same reading frame as that of a target gene present on the genome of the rodent, wherein the poly A addition signal is downstream of the hp7 sequence, wherein the target gene present on the genome of the rodent is an interleukin-6 receptor gene, wherein said foreign gene is a human interleukin-6 receptor gene, and wherein said rodent has a plasma concentration of the protein encoded by said human interleukin-6 receptor gene that is equivalent to the plasma concentration of the protein in healthy humans.

2. The rodent according to claim 1, wherein the rodent is a mouse.

3. The rodent according to claim 1, wherein human interleukin-6 is overexpressed.

4. A method for evaluating the therapeutic effect of a test substance on a disease caused by human interleukin-6 or human interleukin-6 receptor, comprising the steps of:
(a) administering the test substance to a rodent according to claim 3; and
(b) determining whether or not a symptom of the disease caused by human interleukin-6 or human interleukin-6 receptor has been suppressed in the rodent that has received the test substance.

5. The method according to claim 4, wherein the disease caused by human interleukin-6 or human interleukin-6 receptor is Castleman's disease.

6. A method for evaluating the pharmacokinetic properties of a test substance, comprising the steps of:
(a) administering the test substance to a rodent according to claim 1; and
(b) measuring the plasma concentration of the test substance in the rodent that has received the test substance.

7. A method for evaluating a test substance for its activity of removing a soluble human interleukin-6 receptor from blood, comprising the steps of:
(a) administering the test substance to a rodent according to claim 1; and
(b) measuring the plasma concentration of the soluble human interleukin-6 receptor in the rodent that has received the test substance.

8. The method according to claim 7, wherein the test substance is an antibody against human interleukin-6 receptor.

9. A method for producing an antibody against human interleukin-6 receptor having a therapeutic effect on a disease caused by human interleukin-6 or human interleukin-6 receptor, comprising the steps of:
(a) producing each antibody against human interleukin-6 receptor;
(b) administering the antibody to a rodent according to claim 3;
(c) determining whether or not a symptom of the disease caused by human interleukin-6 or human interleukin-6 receptor has been suppressed in the rodent that has received the antibody; and
(d) selecting an antibody that suppresses the symptom of the disease caused by human interleukin-6 or human interleukin-6 receptor.

10. The method according to claim 9, wherein the disease caused by human interleukin-6 or human interleukin-6 receptor is Castleman's disease.

11. A method for producing an antibody against human interleukin-6 receptor having desired pharmacokinetic properties, comprising the steps of:
(a) producing each antibody against human interleukin-6 receptor;
(b) administering the antibody to a rodent according to claim 1;
(c) measuring the plasma concentration of the antibody in the rodent that has received the antibody; and
(d) selecting an antibody having the desired plasma concentration.

12. A method for producing an antibody against human interleukin-6 receptor having an activity of removing a soluble human interleukin-6 receptor from blood, comprising the steps of:
(a) producing each antibody against human interleukin-6 receptor;
(b) administering the antibody to a rodent according to claim 1;
(c) measuring the plasma concentration of the soluble human interleukin-6 receptor in the rodent that has received the antibody; and
(d) selecting an antibody that lowers the plasma concentration of the soluble human interleukin-6 receptor.

13. The method for producing an antibody according to claim 9, further comprising the step of (e) chimerizing or humanizing the selected antibody.

14. A knock-in vector for preparation of a rodent according to claim 1, the vector carrying a DNA comprising an hp7 sequence-encoding DNA and a poly A addition signal-encoding DNA added on the 3' side of a DNA encoding a foreign gene,
wherein said foreign gene is a human interleukin-6 receptor gene, and wherein said rodent has a plasma concentration of the protein encoded by said human interleukin-6 receptor gene that is equivalent to the plasma concentration of the protein in healthy humans.

15. A transformed cell for preparation of a rodent according to claim 1, the transformed cell harboring a knock-in vector carrying a DNA comprising an hp7 sequence-encoding DNA and a poly A addition signal-encoding DNA added on the 3' side of a DNA encoding a foreign gene,
wherein said foreign gene is a human interleukin-6 receptor gene, and wherein said rodent has a plasma concentration of the protein encoded by said human interleukin-6 receptor gene that is equivalent to the plasma concentration of the protein in healthy humans.

16. The rodent according to claim 1, wherein an Frt or a Rox sequence is located downstream of the poly A addition signal.

* * * * *